United States Patent [19]
Chandrashekar et al.

[11] Patent Number: 6,165,735
[45] Date of Patent: Dec. 26, 2000

[54] PARASITIC HELMINTH ASPARAGINASE PROTEINS, NUCLEIC ACID MOLECULES, AND USES THEREOF

[75] Inventors: Ramaswamy Chandrashekar; Naotoshi Tsuji, both of Fort Collins, Colo.

[73] Assignees: Heska Corporation; Colorado State University Research Foundation

[21] Appl. No.: 09/397,979

[22] Filed: Sep. 16, 1999

Related U.S. Application Data

[62] Division of application No. 09/140,177, Aug. 25, 1998, Pat. No. 6,042,825, which is a division of application No. 08/929,501, Sep. 15, 1997, Pat. No. 5,854,051.

[51] Int. Cl.[7] ................... G01N 33/53; G01N 33/569; C07K 16/00; C12P 21/08; A61K 39/395
[52] U.S. Cl. ................... 435/7.22; 530/388.6; 530/389.2; 424/151.1; 424/139.1
[58] Field of Search ................... 435/7.22; 530/388.6; 530/389.2; 424/151.1, 139.1

[56] References Cited

FOREIGN PATENT DOCUMENTS 0 726 313 A2   8/1996   European Pat. Off. .

OTHER PUBLICATIONS

Bussolati et al., 1994, *FASEB Journal* 8(4–5), p. A95, Abstract No. 549.
Dunlop et al., 1978, *The Journal of Biological Chemistry* 253:4, pp. 1297–1304.
Jerlström et al., *Gene 78*, pp. 37–46. 1989.
Mesas et al., 1990, *Journal of General Microbiology 136*, pp. 515–519.
Różalska, Malgorzata, 1989, *Acta Microbiologica Polonica 38*, pp. 233–245.
Sobiś et al., 1991, *Acta Microbiologica Polonica 40:3/4*, pp. 143–452.
Sun et al., 1991, *Journal of Bacteriology 173: 12*, pp. 3831–3845.
Tanaka et al., 1988, *The Journal of Biological Chemistry 263*, pp. 8583–8591.
Tiwari et al., 1996, *Indian Journal of Biochemistry & Biphysics 33*, pp. 371–376.
Tsavdaridis et al., 1991, *Biochemistry International 24:2*, pp. 281–290.
Wilson et al., 1994, *Nature 368*, pp. 32–38.
Zhang et al., 1995, *Comp. Biochem. Pjysiol. 112B:4*, pp. 607–612.
Grantham et al., 1986, *Parasitology*, vol. 93, pp. 481–193.
Dorner et al., 1993, Genbank Accession No. Q41029.
Feng, et al., 1985, *J. Mol. Evol. 21*, pp. 112–125.
Johnson, et al., 1993, *J. Mol. Biol. 233*, pp. 716–738.
Meinkoth, et al., 1984, *Analytical Biochemistry 138*, pp. 267–284.

*Primary Examiner*—Christina Y. Chan
*Assistant Examiner*—Gerald R. Ewoldt
*Attorney, Agent, or Firm*—Heska Corporation

[57] ABSTRACT

The present invention relates to: parasitic helminth asparaginase proteins; parasitic helminth asparaginase nucleic acid molecules, including those that encode such asparaginase proteins; antibodies raised against such asparaginase proteins; and compounds that inhibit parasitic helminth asparaginase activity. The present invention also includes methods to obtain such proteins, nucleic acid molecules, antibodies, and inhibitory compounds. Also included in the present invention are therapeutic compositions comprising such proteins, nucleic acid molecules, antibodies and/or inhibitory compounds as well as the use of such therapeutic compositions to protect animals from diseases caused by parasitic helminths.

6 Claims, No Drawings

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
       (A) LENGTH: 1753 nucleotides
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: CDS
       (B) LOCATION: 1..1518

(xi) SEQUENCE DESCRIPTION: SEQ ID NO:1:

```
GAT TCA TCA GAT ATG ACA TTT GAT GAC TGG ATT CAT ATC GGT            42
Asp Ser Ser Asp Met Thr Phe Asp Asp Trp Ile His Ile Gly
1               5                   10

AAA GAT ATT CAA AGA GCT TAC GAT CAA TAT GTG GGC TTT GTT            84
Lys Asp Ile Gln Arg Ala Tyr Asp Gln Tyr Val Gly Phe Val
15                  20                  25

ATA TTA CAT GGT ACT GAT ACA CTG GCA TAT ACG GCA TGT GCT           126
Ile Leu His Gly Thr Asp Thr Leu Ala Tyr Thr Ala Cys Ala
30                  35                  40

TTG TCA TTT ATG CTG GAG AAC GTA AGA AAA CCC ATT GTT ATT           168
Leu Ser Phe Met Leu Glu Asn Val Arg Lys Pro Ile Val Ile
45                  50                  55

ACA GGA GCT CAA ATA CCA GTG TGT GAA GTT CGT TCT GAC GGT           210
Thr Gly Ala Gln Ile Pro Val Cys Glu Val Arg Ser Asp Gly
60                  65                  70

CGA GAA AAT TTG ATT GGT GCA CTG ATT ATT GCA GCC AAT TAT           252
Arg Glu Asn Leu Ile Gly Ala Leu Ile Ile Ala Ala Asn Tyr
75                  80

GAT ATT CCT GAA GTT ACT GTA TAT TTC AAT AAT AAG CTG TTT           294
Asp Ile Pro Glu Val Thr Val Tyr Phe Asn Asn Lys Leu Phe
85                  90                  95

CGA GGA AAT CGT ACA GTA AAA ATA GAT AAC AGA TCA ATG GAT           336
Arg Gly Asn Arg Thr Val Lys Ile Asp Asn Arg Ser Met Asp
100                 105                 110

GCT TTT GAA AGT CCA AAT ATG CTT CCA ATT GCT TAC ATG GAT           378
Ala Phe Glu Ser Pro Asn Met Leu Pro Ile Ala Tyr Met Asp
115                 120                 125

GTT GAT ATA AAA GTT AAT TAT GAT TCA ATA TTT CGT TCA CCA           420
Val Asp Ile Lys Val Asn Tyr Asp Ser Ile Phe Arg Ser Pro
130                 135                 140

TCA ATG GCT CCA TTC GTA GTA CAC GAC CAA TTA TGT CGA AAT           462
Ser Met Ala Pro Phe Val Val His Asp Gln Leu Cys Arg Asn
145                 150

GTT GGA TTG TTG AGA ATT TTT CCA TCG ATG TCT ATA GAA AAC           504
Val Gly Leu Leu Arg Ile Phe Pro Ser Met Ser Ile Glu Asn
155                 160                 165

GTT AGA GCA TCC TTG CAG GCA CCT ATT GAA GGT GTT GTT CTG           546
Val Arg Ala Ser Leu Gln Ala Pro Ile Glu Gly Val Val Leu
170                 175                 180

CAG ACG TTT GGT GCT GGT AAT ATG CCC TCC CAT AGG ACA GAT           588
Gln Thr Phe Gly Ala Gly Asn Met Pro Ser His Arg Thr Asp
185                 190                 195
```

```
ATA ATC GAT GAA TTG AAA AAA GCT GTT GAT CGA GGA TGT ATT          630
Ile Ile Asp Glu Leu Lys Lys Ala Val Asp Arg Gly Cys Ile
200             205                 210

ATT ATT AAT TGC TCA CAG TGT GTC CGT GGA CAA GTA GAT ATT          672
Ile Ile Asn Cys Ser Gln Cys Val Arg Gly Gln Val Asp Ile
215             220

CAT TAT TTA ACG GGA AAG GTT CTA TAC GAC ATG GGA ATT ATT          714
His Tyr Leu Thr Gly Lys Val Leu Tyr Asp Met Gly Ile Ile
225             230                 235

CCT GGT TCA GAT ATG ACT GCA GAA GCA GCA TTA ACA AAA TTA          756
Pro Gly Ser Asp Met Thr Ala Glu Ala Ala Leu Thr Lys Leu
240             245                 250

TCG TAT GTA TTG AGC AAA GAT TGT TGG GAA CTT GTG GAG AAA          798
Ser Tyr Val Leu Ser Lys Asp Cys Trp Glu Leu Val Glu Lys
255             260                 265

AAA GCA ATG ATG GTT AAA AAT ATC AGA GGC GAA TTA ACT GTT          840
Lys Ala Met Met Val Lys Asn Ile Arg Gly Glu Leu Thr Val
270             275                 280

GCA AAA GCA GAA CCA CTC AAA GAT CTA GAA ATC GTA TCA CAG          882
Ala Lys Ala Glu Pro Leu Lys Asp Leu Glu Ile Val Ser Gln
285             290

ATG GCA AGA TTC CTG CAT CTA AGT TCT TCT CAT GAA ATG AAA          924
Met Ala Arg Phe Leu His Leu Ser Ser Ser His Glu Met Lys
295             300                 305

CTC CTC TGT CAT GCT ATT TTT CCA CAA TTA TTG TGT TAT GCA          966
Leu Leu Cys His Ala Ile Phe Pro Gln Leu Leu Cys Tyr Ala
310             315                 320

GCT AGT AAT GGG GAT ATC GAA ATG CTA AAG GCA CTT CAT GAA         1008
Ala Ser Asn Gly Asp Ile Glu Met Leu Lys Ala Leu His Glu
325             330                 335

AAT GGA GTT GAT CTT TCG GTT GTT GAC TAT AAT GGA CGC AAT         1050
Asn Gly Val Asp Leu Ser Val Val Asp Tyr Asn Gly Arg Asn
340             345                 350

GCT TTG CAT GTA GCA GCG AGT GCA GGT CAC GTT GGT GCT GTC         1092
Ala Leu His Val Ala Ala Ser Ala Gly His Val Gly Ala Val
355             360

AAA TAT CTG TTG ACC CAA GGT GTT AGT TTT CAT CTG AGA GAT         1134
Lys Tyr Leu Leu Thr Gln Gly Val Ser Phe His Leu Arg Asp
365             370                 375

CAA TGG GAT GAG AAT GCC CTC GTA AGT GCA GTA AAA ATG AAA         1176
Gln Trp Asp Glu Asn Ala Leu Val Ser Ala Val Lys Met Lys
380             385                 390

AAT AAG ATC TTA ATT GAA ACT TTG CGA TCT GCA GGG GCA CTG         1218
Asn Lys Ile Leu Ile Glu Thr Leu Arg Ser Ala Gly Ala Leu
395             400                 405

CTT TCC ATA AAT TCA CGC AGA TTA GGT GTT GAA CTA TGT CTA         1260
Leu Ser Ile Asn Ser Arg Arg Leu Gly Val Glu Leu Cys Leu
410             415                 420

TGT GCC AGC TAT GGC GAC ACG GAA ACA CTG AAT TCT TGG CTT         1302
Cys Ala Ser Tyr Gly Asp Thr Glu Thr Leu Asn Ser Trp Leu
425             430

GCT GCC GGA GCC GAT ATA AAT CAA CAA GAT TAC AAT GGC GAA         1344
Ala Ala Gly Ala Asp Ile Asn Gln Gln Asp Tyr Asn Gly Glu
435             440                 445

ACT GCT TTG CAT ATT GCG GTG AAA TCG AGA AAT AAG CAA TTG         1386
Thr Ala Leu His Ile Ala Val Lys Ser Arg Asn Lys Gln Leu
450             455                 460

GTA CAT TAT TTG CTG GAT AGA GAT GCA GAT CCA TAC AAA ATT         1428
Val His Tyr Leu Leu Asp Arg Asp Ala Asp Pro Tyr Lys Ile
```

-continued

```
                465                 470                 475
GAC GAT TTT AAT TTA ACG CCT CTT AGA CAT GCT AAA AAA CTT              1470
Asp Asp Phe Asn Leu Thr Pro Leu Arg His Ala Lys Lys Leu
480                 485                 490

AAT TTA CAA GAT CTA GTC ATT AGA ATG AAA AAG ATG AAA AAA              1512
Asn Leu Gln Asp Leu Val Ile Arg Met Lys Lys Met Lys Lys
495                 500

GTT CAG TAA TGTTGCTGCA GAAAATAAAG ATCTTATGCA CTCAGAATGT              1561
Val Gln
505

ATTCAGAAGT ATGGTACAAA AGCCTTAAAT TATGCTAGAT CTTGCATGAT               1611

TTCTAGCTTT TTAAATGGTA ATTTTTGTTC CGTCTTTTTT CGCAAAGACT               1661

GATATAATTT AATGAAAAAA AACCTTGTTT ATTCATCGAT TCCTTTTTTA               1711

AACAAAATAG TATTTAATGG CTAAAAAAAA AAAAAAAAAA AA                       1753

(2) INFORMATION FOR SEQ ID NO:2:

(i) SEQUENCE CHARACTERISTICS:
        (A) LENGTH:  506 amino acids
        (B) TYPE:  amino acid
        (D) TOPOLOGY:  linear (ii) MOLECULE TYPE:  Protein (xi) SEQUENCE DESCRIPTION:  SEQ ID NO:2:

Asp Ser Ser Asp Met Thr Phe Asp Asp Trp Ile His Ile Gly
1               5                   10

Lys Asp Ile Gln Arg Ala Tyr Asp Gln Tyr Val Gly Phe Val
15                  20                  25

Ile Leu His Gly Thr Asp Thr Leu Ala Tyr Thr Ala Cys Ala
30                  35                  40

Leu Ser Phe Met Leu Glu Asn Val Arg Lys Pro Ile Val Ile
45                  50                  55

Thr Gly Ala Gln Ile Pro Val Cys Glu Val Arg Ser Asp Gly
60                  65                  70

Arg Glu Asn Leu Ile Gly Ala Leu Ile Ile Ala Ala Asn Tyr
75                  80

Asp Ile Pro Glu Val Thr Val Tyr Phe Asn Asn Lys Leu Phe
85                  90                  95

Arg Gly Asn Arg Thr Val Lys Ile Asp Asn Arg Ser Met Asp
100                 105                 110

Ala Phe Glu Ser Pro Asn Met Leu Pro Ile Ala Tyr Met Asp
115                 120                 125

Val Asp Ile Lys Val Asn Tyr Asp Ser Ile Phe Arg Ser Pro
130                 135                 140

Ser Met Ala Pro Phe Val His Asp Gln Leu Cys Arg Asn
145                 150

Val Gly Leu Leu Arg Ile Phe Pro Ser Met Ser Ile Glu Asn
155                 160                 165

Val Arg Ala Ser Leu Gln Ala Pro Ile Glu Gly Val Val Leu
170                 175                 180

Gln Thr Phe Gly Ala Gly Asn Met Pro Ser His Arg Thr Asp
185                 190                 195

Ile Ile Asp Glu Leu Lys Lys Ala Val Asp Arg Gly Cys Ile
200                 205                 210
```

```
Ile Ile Asn Cys Ser Gln Cys Val Arg Gly Gln Val Asp Ile
215                 220

His Tyr Leu Thr Gly Lys Val Leu Tyr Asp Met Gly Ile Ile
225                 230                 235

Pro Gly Ser Asp Met Thr Ala Glu Ala Ala Leu Thr Lys Leu
240                 245                 250

Ser Tyr Val Leu Ser Lys Asp Cys Trp Glu Leu Val Glu Lys
255                 260                 265

Lys Ala Met Met Val Lys Asn Ile Arg Gly Glu Leu Thr Val
270                 275                 280

Ala Lys Ala Glu Pro Leu Lys Asp Leu Glu Ile Val Ser Gln
285                 290

Met Ala Arg Phe Leu His Leu Ser Ser Ser His Glu Met Lys
295                 300                 305

Leu Leu Cys His Ala Ile Phe Pro Gln Leu Leu Cys Tyr Ala
310                 315                 320

Ala Ser Asn Gly Asp Ile Glu Met Leu Lys Ala Leu His Glu
325                 330                 335

Asn Gly Val Asp Leu Ser Val Val Asp Tyr Asn Gly Arg Asn
340                 345                 350

Ala Leu His Val Ala Ala Ser Ala Gly His Val Gly Ala Val
355                 360

Lys Tyr Leu Leu Thr Gln Gly Val Ser Phe His Leu Arg Asp
365                 370                 375

Gln Trp Asp Glu Asn Ala Leu Val Ser Ala Val Lys Met Lys
380                 385                 390

Asn Lys Ile Leu Ile Glu Thr Leu Arg Ser Ala Gly Ala Leu
395                 400                 405

Leu Ser Ile Asn Ser Arg Arg Leu Gly Val Glu Leu Cys Leu
410                 415                 420

Cys Ala Ser Tyr Gly Asp Thr Glu Thr Leu Asn Ser Trp Leu
425                 430

Ala Ala Gly Ala Asp Ile Asn Gln Gln Asp Tyr Asn Gly Glu
435                 440                 445

Thr Ala Leu His Ile Ala Val Lys Ser Arg Asn Lys Gln Leu
450                 455                 460

Val His Tyr Leu Leu Asp Arg Asp Ala Asp Pro Tyr Lys Ile
465                 470                 475

Asp Asp Phe Asn Leu Thr Pro Leu Arg His Ala Lys Lys Leu
480                 485                 490

Asn Leu Gln Asp Leu Val Ile Arg Met Lys Lys Met Lys Lys
495                 500

Val Gln
505
```

(2) INFORMATION FOR SEQ ID NO:3:

(i) SEQUENCE CHARACTERISTICS:
        (A) LENGTH: 1753 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

-continued

| | |
|---|---|
| TTTTTTTTTT TTTTTTTTTT AGCCATTAAA TACTATTTTG TTTAAAAAAG | 50 |
| GAATCGATGA ATAAACAAGG TTTTTTTTCA TTAAATTATA TCAGTCTTTG | 100 |
| CGAAAAAAGA CGGAACAAAA ATTACCATTT AAAAAGCTAG AAATCATGCA | 150 |
| AGATCTAGCA TAATTTAAGG CTTTTGTACC ATACTTCTGA ATACATTCTG | 200 |
| AGTGCATAAG ATCTTTATTT TCTGCAGCAA CATTACTGAA CTTTTTTCAT | 250 |
| CTTTTTCATT CTAATGACTA GATCTTGTAA ATTAAGTTTT TTAGCATGTC | 300 |
| TAAGAGGCGT TAAATTAAAA TCGTCAATTT TGTATGGATC TGCATCTCTA | 350 |
| TCCAGCAAAT AATGTACCAA TTGCTTATTT CTCGATTTCA CCGCAATATG | 400 |
| CAAAGCAGTT TCGCCATTGT AATCTTGTTG ATTTATATCG GCTCCGGCAG | 450 |
| CAAGCCAAGA ATTCAGTGTT TCCGTGTCGC CATAGCTGGC ACATAGACAT | 500 |
| AGTTCAACAC CTAATCTGCG TGAATTTATG GAAAGCAGTG CCCCTGCAGA | 550 |
| TCGCAAAGTT TCAATTAAGA TCTTATTTTT CATTTTTACT GCACTTACGA | 600 |
| GGGCATTCTC ATCCCATTGA TCTCTCAGAT GAAAACTAAC ACCTTGGGTC | 650 |
| AACAGATATT TGACAGCACC AACGTGACCT GCACTCGCTG CTACATGCAA | 700 |
| AGCATTGCGT CCATTATAGT CAACAACCGA AAGATCAACT CCATTTTCAT | 750 |
| GAAGTGCCTT TAGCATTTCG ATATCCCCAT TACTAGCTGC ATAACACAAT | 800 |
| AATTGTGGAA AAATAGCATG ACAGAGGAGT TTCATTTCAT GAGAAGAACT | 850 |
| TAGATGCAGG AATCTTGCCA TCTGTGATAC GATTTCTAGA TCTTTGAGTG | 900 |
| GTTCTGCTTT TGCAACAGTT AATTCGCCTC TGATATTTTT AACCATCATT | 950 |
| GCTTTTTTCT CCACAAGTTC CCAACAATCT TTGCTCAATA CATACGATAA | 1000 |
| TTTTGTTAAT GCTGCTTCTG CAGTCATATC TGAACCAGGA ATAATTCCCA | 1050 |
| TGTCGTATAG AACCTTTCCC GTTAAATAAT GAATATCTAC TTGTCCACGG | 1100 |
| ACACACTGTG AGCAATTAAT AATAATACAT CCTCGATCAA CAGCTTTTTT | 1150 |
| CAATTCATCG ATTATATCTG TCCTATGGGA GGGCATATTA CCAGCACCAA | 1200 |
| ACGTCTGCAG AACAACACCT TCAATAGGTG CCTGCAAGGA TGCTCTAACG | 1250 |
| TTTTCTATAG ACATCGATGG AAAAATTCTC AACAATCCAA CATTTCGACA | 1300 |
| TAATTGGTCG TGTACTACGA ATGGAGCCAT TGATGGTGAA CGAAATATTG | 1350 |
| AATCATAATT AACTTTTATA TCAACATCCA TGTAAGCAAT TGGAAGCATA | 1400 |
| TTTGGACTTT CAAAAGCATC CATTGATCTG TTATCTATTT TTACTGTACG | 1450 |
| ATTTCCTCGA AACAGCTTAT TATTGAAATA TACAGTAACT TCAGGAATAT | 1500 |
| CATAATTGGC TGCAATAATC AGTGCACCAA TCAAATTTTC TCGACCGTCA | 1550 |
| GAACGAACTT CACACACTGG TATTTGAGCT CCTGTAATAA CAATGGGTTT | 1600 |
| TCTTACGTTC TCCAGCATAA ATGACAAAGC ACATGCCGTA TATGCCAGTG | 1650 |
| TATCAGTACC ATGTAATATA ACAAAGCCCA CATATTGATC GTAAGCTCTT | 1700 |
| TGAATATCTT TACCGATATG AATCCAGTCA TCAAATGTCA TATCTGATGA | 1750 |
| ATC | 1753 |

(2) INFORMATION FOR SEQ ID NO:4:

(i) SEQUENCE CHARACTERISTICS:
        (A) LENGTH: 1518 nucleotides
        (B) TYPE: nucleic acid
        (C) STRANDEDNESS: single

```
        (D) TOPOLOGY: linear (ii) MOLECULE TYPE: cDNA (ix) FEATURE:
         (A) NAME/KEY: CDS
         (B) LOCATION: 1..1518

(xi) SEQUENCE DESCRIPTION: SEQ ID NO:4:

GAT TCA TCA GAT ATG ACA TTT GAT GAC TGG ATT CAT ATC GGT              42
Asp Ser Ser Asp Met Thr Phe Asp Asp Trp Ile His Ile Gly
1               5                   10

AAA GAT ATT CAA AGA GCT TAC GAT CAA TAT GTG GGC TTT GTT              84
Lys Asp Ile Gln Arg Ala Tyr Asp Gln Tyr Val Gly Phe Val
15                  20                  25

ATA TTA CAT GGT ACT GAT ACA CTG GCA TAT ACG GCA TGT GCT             126
Ile Leu His Gly Thr Asp Thr Leu Ala Tyr Thr Ala Cys Ala
30                  35                  40

TTG TCA TTT ATG CTG GAG AAC GTA AGA AAA CCC ATT GTT ATT             168
Leu Ser Phe Met Leu Glu Asn Val Arg Lys Pro Ile Val Ile
45                  50                  55

ACA GGA GCT CAA ATA CCA GTG TGT GAA GTT CGT TCT GAC GGT             210
Thr Gly Ala Gln Ile Pro Val Cys Glu Val Arg Ser Asp Gly
60                  65                  70

CGA GAA AAT TTG ATT GGT GCA CTG ATT ATT GCA GCC AAT TAT             252
Arg Glu Asn Leu Ile Gly Ala Leu Ile Ile Ala Ala Asn Tyr
75                  80

GAT ATT CCT GAA GTT ACT GTA TAT TTC AAT AAT AAG CTG TTT             294
Asp Ile Pro Glu Val Thr Val Tyr Phe Asn Asn Lys Leu Phe
85                  90                  95

CGA GGA AAT CGT ACA GTA AAA ATA GAT AAC AGA TCA ATG GAT             336
Arg Gly Asn Arg Thr Val Lys Ile Asp Asn Arg Ser Met Asp
100                 105                 110

GCT TTT GAA AGT CCA AAT ATG CTT CCA ATT GCT TAC ATG GAT             378
Ala Phe Glu Ser Pro Asn Met Leu Pro Ile Ala Tyr Met Asp
115                 120                 125

GTT GAT ATA AAA GTT AAT TAT GAT TCA ATA TTT CGT TCA CCA             420
Val Asp Ile Lys Val Asn Tyr Asp Ser Ile Phe Arg Ser Pro
130                 135                 140

TCA ATG GCT CCA TTC GTA GTA CAC GAC CAA TTA TGT CGA AAT             462
Ser Met Ala Pro Phe Val Val His Asp Gln Leu Cys Arg Asn
145                 150

GTT GGA TTG TTG AGA ATT TTT CCA TCG ATG TCT ATA GAA AAC             504
Val Gly Leu Leu Arg Ile Phe Pro Ser Met Ser Ile Glu Asn
155                 160                 165

GTT AGA GCA TCC TTG CAG GCA CCT ATT GAA GGT GTT GTT CTG             546
Val Arg Ala Ser Leu Gln Ala Pro Ile Glu Gly Val Val Leu
170                 175                 180

CAG ACG TTT GGT GCT GGT AAT ATG CCC TCC CAT AGG ACA GAT             588
Gln Thr Phe Gly Ala Gly Asn Met Pro Ser His Arg Thr Asp
185                 190                 195

ATA ATC GAT GAA TTG AAA AAA GCT GTT GAT CGA GGA TGT ATT             630
Ile Ile Asp Glu Leu Lys Lys Ala Val Asp Arg Gly Cys Ile
200                 205                 210

ATT ATT AAT TGC TCA CAG TGT GTC CGT GGA CAA GTA GAT ATT             672
Ile Ile Asn Cys Ser Gln Cys Val Arg Gly Gln Val Asp Ile
215                 220

CAT TAT TTA ACG GGA AAG GTT CTA TAC GAC ATG GGA ATT ATT             714
His Tyr Leu Thr Gly Lys Val Leu Tyr Asp Met Gly Ile Ile
225                 230                 235

CCT GGT TCA GAT ATG ACT GCA GAA GCA GCA TTA ACA AAA TTA             756
```

```
                        -continued

Pro Gly Ser Asp Met Thr Ala Glu Ala Ala Leu Thr Lys Leu
240                 245                 250

TCG TAT GTA TTG AGC AAA GAT TGT TGG GAA CTT GTG GAG AAA        798
Ser Tyr Val Leu Ser Lys Asp Cys Trp Glu Leu Val Glu Lys
255                 260                 265

AAA GCA ATG ATG GTT AAA AAT ATC AGA GGC GAA TTA ACT GTT        840
Lys Ala Met Met Val Lys Asn Ile Arg Gly Glu Leu Thr Val
270                 275                 280

GCA AAA GCA GAA CCA CTC AAA GAT CTA GAA ATC GTA TCA CAG        882
Ala Lys Ala Glu Pro Leu Lys Asp Leu Glu Ile Val Ser Gln
285                 290

ATG GCA AGA TTC CTG CAT CTA AGT TCT TCT CAT GAA ATG AAA        924
Met Ala Arg Phe Leu His Leu Ser Ser Ser His Glu Met Lys
295                 300                 305

CTC CTC TGT CAT GCT ATT TTT CCA CAA TTA TTG TGT TAT GCA        966
Leu Leu Cys His Ala Ile Phe Pro Gln Leu Leu Cys Tyr Ala
310                 315                 320

GCT AGT AAT GGG GAT ATC GAA ATG CTA AAG GCA CTT CAT GAA       1008
Ala Ser Asn Gly Asp Ile Glu Met Leu Lys Ala Leu His Glu
325                 330                 335

AAT GGA GTT GAT CTT TCG GTT GTT GAC TAT AAT GGA CGC AAT       1050
Asn Gly Val Asp Leu Ser Val Val Asp Tyr Asn Gly Arg Asn
340                 345                 350

GCT TTG CAT GTA GCA GCG AGT GCA GGT CAC GTT GGT GCT GTC       1092
Ala Leu His Val Ala Ala Ser Ala Gly His Val Gly Ala Val
355                 360

AAA TAT CTG TTG ACC CAA GGT GTT AGT TTT CAT CTG AGA GAT       1134
Lys Tyr Leu Leu Thr Gln Gly Val Ser Phe His Leu Arg Asp
365                 370                 375

CAA TGG GAT GAG AAT GCC CTC GTA AGT GCA GTA AAA ATG AAA       1176
Gln Trp Asp Glu Asn Ala Leu Val Ser Ala Val Lys Met Lys
380                 385                 390

AAT AAG ATC TTA ATT GAA ACT TTG CGA TCT GCA GGG GCA CTG       1218
Asn Lys Ile Leu Ile Glu Thr Leu Arg Ser Ala Gly Ala Leu
395                 400                 405

CTT TCC ATA AAT TCA CGC AGA TTA GGT GTT GAA CTA TGT CTA       1260
Leu Ser Ile Asn Ser Arg Arg Leu Gly Val Glu Leu Cys Leu
410                 415                 420

TGT GCC AGC TAT GGC GAC ACG GAA ACA CTG AAT TCT TGG CTT       1302
Cys Ala Ser Tyr Gly Asp Thr Glu Thr Leu Asn Ser Trp Leu
425                 430

GCT GCC GGA GCC GAT ATA AAT CAA CAA GAT TAC AAT GGC GAA       1344
Ala Ala Gly Ala Asp Ile Asn Gln Gln Asp Tyr Asn Gly Glu
435                 440                 445

ACT GCT TTG CAT ATT GCG GTG AAA TCG AGA AAT AAG CAA TTG       1386
Thr Ala Leu His Ile Ala Val Lys Ser Arg Asn Lys Gln Leu
450                 455                 460

GTA CAT TAT TTG CTG GAT AGA GAT GCA GAT CCA TAC AAA ATT       1428
Val His Tyr Leu Leu Asp Arg Asp Ala Asp Pro Tyr Lys Ile
465                 470                 475

GAC GAT TTT AAT TTA ACG CCT CTT AGA CAT GCT AAA AAA CTT       1470
Asp Asp Phe Asn Leu Thr Pro Leu Arg His Ala Lys Lys Leu
480                 485                 490

AAT TTA CAA GAT CTA GTC ATT AGA ATG AAA AAG ATG AAA AAA       1512
Asn Leu Gln Asp Leu Val Ile Arg Met Lys Lys Met Lys Lys
495                 500

GTT CAG                                                       1518
Val Gln
505
```

(2) INFORMATION FOR SEQ ID NO:5:

(i) SEQUENCE CHARACTERISTICS:
        (A) LENGTH: 1518 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
CTGAACTTTT TTCATCTTTT TCATTCTAAT GACTAGATCT TGTAAATTAA          50
GTTTTTTAGC ATGTCTAAGA GGCGTTAAAT TAAAATCGTC AATTTTGTAT         100
GGATCTGCAT CTCTATCCAG CAAATAATGT ACCAATTGCT TATTTCTCGA         150
TTTCACCGCA ATATGCAAAG CAGTTTCGCC ATTGTAATCT TGTTGATTTA         200
TATCGGCTCC GGCAGCAAGC CAAGAATTCA GTGTTTCCGT GTCGCCATAG         250
CTGGCACATA GACATAGTTC AACACCTAAT CTGCGTGAAT TTATGGAAAG         300
CAGTGCCCCT GCAGATCGCA AAGTTTCAAT TAAGATCTTA TTTTTCATTT         350
TTACTGCACT TACGAGGGCA TTCTCATCCC ATTGATCTCT CAGATGAAAA         400
CTAACACCTT GGGTCAACAG ATATTTGACA GCACCAACGT GACCTGCACT         450
CGCTGCTACA TGCAAAGCAT TGCGTCCATT ATAGTCAACA ACCGAAAGAT         500
CAACTCCATT TTCATGAAGT GCCTTTAGCA TTTCGATATC CCCATTACTA         550
GCTGCATAAC ACAATAATTG TGGAAAAATA GCATGACAGA GGAGTTTCAT         600
TTCATGAGAA GAACTTAGAT GCAGGAATCT TGCCATCTGT GATACGATTT         650
CTAGATCTTT GAGTGGTTCT GCTTTTGCAA CAGTTAATTC GCCTCTGATA         700
TTTTTAACCA TCATTGCTTT TTTCTCCACA AGTTCCCAAC AATCTTTGCT         750
CAATACATAC GATAATTTTG TTAATGCTGC TTCTGCAGTC ATATCTGAAC         800
CAGGAATAAT TCCCATGTCG TATAGAACCT TTCCCGTTAA ATAATGAATA         850
TCTACTTGTC CACGGACACA CTGTGAGCAA TTAATAATAA TACATCCTCG         900
ATCAACAGCT TTTTTCAATT CATCGATTAT ATCTGTCCTA TGGGAGGGCA         950
TATTACCAGC ACCAAACGTC TGCAGAACAA CACCTTCAAT AGGTGCCTGC        1000
AAGGATGCTC TAACGTTTTC TATAGACATC GATGGAAAAA TTCTCAACAA        1050
TCCAACATTT CGACATAATT GGTCGTGTAC TACGAATGGA GCCATTGATG        1100
GTGAACGAAA TATTGAATCA TAATTAACTT TTATATCAAC ATCCATGTAA        1150
GCAATTGGAA GCATATTTGG ACTTTCAAAA GCATCCATTG ATCTGTTATC        1200
TATTTTTACT GTACGATTTC CTCGAAACAG CTTATTATTG AAATATACAG        1250
TAACTTCAGG AATATCATAA TTGGCTGCAA TAATCAGTGC ACCAATCAAA        1300
TTTTCTCGAC CGTCAGAACG AACTTCACAC ACTGGTATTT GAGCTCCTGT        1350
AATAACAATG GGTTTTCTTA CGTTCTCCAG CATAAATGAC AAAGCACATG        1400
CCGTATATGC CAGTGTATCA GTACCATGTA ATATAACAAA GCCCACATAT        1450
TGATCGTAAG CTCTTTGAAT ATCTTTACCG ATATGAATCC AGTCATCAAA        1500
TGTCATATCT GATGAATC                                          1518
```

(2) INFORMATION FOR SEQ ID NO:6:

(i) SEQUENCE CHARACTERISTICS:

(A) LENGTH:  439 nucleotides
    (B) TYPE:  nucleic acid
    (C) STRANDEDNESS:  single
    (D) TOPOLOGY:  linear (ii) MOLECULE TYPE:  cDNA (ix) FEATURE:
    (A) NAME/KEY:  CDS
    (B) LOCATION:  69..437

(xi) SEQUENCE DESCRIPTION:  SEQ ID NO:6:

```
GGTTTAATTA CCCAAGTTTG AGCAATTAAA TTAGATTGGA AGTATTTATA              50

CAAATATCAT TCAGTCCG ATG CAG TGT GAA GAA GCG CAT GTT TTA             95
                    Met Gln Cys Glu Glu Ala His Val Leu
                    1               5

GTG CTA TAT ACA GGT GGA ACG ATT GGG ATG AAA TAC ATT GAT            137
Val Leu Tyr Thr Gly Gly Thr Ile Gly Met Lys Tyr Ile Asp
 10              15                  20

GGA GTG TAT CAG CCA GAA GCT AAT TAT CTT CTG CAT GCC ATA            179
Gly Val Tyr Gln Pro Glu Ala Asn Tyr Leu Leu His Ala Ile
 25              30                  35

CGT GAT TTA TCA CTA TTA AAC GAT GAT GAT TAT GTG TCC ACA            221
Arg Asp Leu Ser Leu Leu Asn Asp Asp Asp Tyr Val Ser Thr
 40              45                  50

TAT TAT TCT GAC GCC GAA ATA AGG CCA TAT TGT TTG CCA CCA            263
Tyr Tyr Ser Asp Ala Glu Ile Arg Pro Tyr Cys Leu Pro Pro
 55              60                  65

CTA CAA CAT TCA AAA AAA CGT GTT GTT TAT TGG ATG ATC GAA            305
Leu Gln His Ser Lys Lys Arg Val Val Tyr Trp Met Ile Glu
 70              75

TAT GAT CCA CTT TTG GAT TCA TCA GAT ATG ACA TTT GAT GAC            347
Tyr Asp Pro Leu Leu Asp Ser Ser Asp Met Thr Phe Asp Asp
 80              85                  90

TGG ATT CAT ATC GGT AAA GAT ATT CAA AGA GCT TAC GAT CAA            389
Trp Ile His Ile Gly Lys Asp Ile Gln Arg Ala Tyr Asp Gln
 95             100                 105

TAT GTG GGC TTT GTT ATA TTA CAT GGT ACT GAT ACA CTG GCA            431
Tyr Val Gly Phe Val Ile Leu His Gly Thr Asp Thr Leu Ala
110             115                 120

TAT ACG GC                                                         439
Tyr Thr
```

(2) INFORMATION FOR SEQ ID NO:7:

(i) SEQUENCE CHARACTERISTICS:
        (A) LENGTH:  123 amino acids
        (B) TYPE:  amino acid
        (D) TOPOLOGY:  linear (ii) MOLECULE TYPE:  Protein (xi) SEQUENCE DESCRIPTION:  SEQ ID NO:7:

Met Gln Cys Glu Glu Ala His Val Leu Val Leu Tyr Thr Gly
1               5                   10

Gly Thr Ile Gly Met Lys Tyr Ile Asp Gly Val Tyr Gln Pro
 15              20                  25

Glu Ala Asn Tyr Leu Leu His Ala Ile Arg Asp Leu Ser Leu
 30              35                  40

Leu Asn Asp Asp Asp Tyr Val Ser Thr Tyr Tyr Ser Asp Ala
 45              50                  55

Glu Ile Arg Pro Tyr Cys Leu Pro Pro Leu Gln His Ser Lys

```
                    60                  65                  70
Lys Arg Val Val Tyr Trp Met Ile Glu Tyr Asp Pro Leu Leu
75                  80

Asp Ser Ser Asp Met Thr Phe Asp Asp Trp Ile His Ile Gly
85                  90                  95

Lys Asp Ile Gln Arg Ala Tyr Asp Gln Tyr Val Gly Phe Val
100                 105                 110

Ile Leu His Gly Thr Asp Thr Leu Ala Tyr Thr
115                 120

(2) INFORMATION FOR SEQ ID NO:8:

(i) SEQUENCE CHARACTERISTICS:
        (A) LENGTH: 439 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

GCCGTATATG CCAGTGTATC AGTACCATGT AATATAACAA AGCCCACATA                50

TTGATCGTAA GCTCTTTGAA TATCTTTACC GATATGAATC CAGTCATCAA               100

ATGTCATATC TGATGAATCC AAAAGTGGAT CATATTCGAT CATCCAATAA               150

ACAACACGTT TTTTTGAATG TTGTAGTGGT GGCAAACAAT ATGGCCTTAT               200

TTCGGCGTCA GAATAATATG TGGACACATA ATCATCATCG TTTAATAGTG               250

ATAAATCACG TATGGCATGC AGAAGATAAT TAGCTTCTGG CTGATACACT               300

CCATCAATGT ATTTCATCCC AATCGTTCCA CCTGTATATA GCACTAAAAC               350

ATGCGCTTCT TCACACTGCA TCGGACTGAA TGATATTTGT ATAAATACTT               400

CCAATCTAAT TTAATTGCTC AAACTTGGGT AATTAAACC                           439

(2) INFORMATION FOR SEQ ID NO:9:

(i) SEQUENCE CHARACTERISTICS:
        (A) LENGTH: 369 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..369

(xi) SEQUENCE DESCRIPTION: SEQ ID NO:9:

ATG CAG TGT GAA GAA GCG CAT GTT TTA GTG CTA TAT ACA GGT              42
Met Gln Cys Glu Glu Ala His Val Leu Val Leu Tyr Thr Gly
1               5                   10

GGA ACG ATT GGG ATG AAA TAC ATT GAT GGA GTG TAT CAG CCA              84
Gly Thr Ile Gly Met Lys Tyr Ile Asp Gly Val Tyr Gln Pro
15                  20                  25

GAA GCT AAT TAT CTT CTG CAT GCC ATA CGT GAT TTA TCA CTA             126
Glu Ala Asn Tyr Leu Leu His Ala Ile Arg Asp Leu Ser Leu
30                  35                  40

TTA AAC GAT GAT GAT TAT GTG TCC ACA TAT TAT TCT GAC GCC             168
Leu Asn Asp Asp Asp Tyr Val Ser Thr Tyr Tyr Ser Asp Ala
45                  50                  55

GAA ATA AGG CCA TAT TGT TTG CCA CCA CTA CAA CAT TCA AAA             210
```

-continued

```
Glu Ile Arg Pro Tyr Cys Leu Pro Pro Leu Gln His Ser Lys
 60              65                  70

AAA CGT GTT GTT TAT TGG ATG ATC GAA TAT GAT CCA CTT TTG        252
Lys Arg Val Val Tyr Trp Met Ile Glu Tyr Asp Pro Leu Leu
 75              80

GAT TCA TCA GAT ATG ACA TTT GAT GAC TGG ATT CAT ATC GGT        294
Asp Ser Ser Asp Met Thr Phe Asp Asp Trp Ile His Ile Gly
 85              90                  95

AAA GAT ATT CAA AGA GCT TAC GAT CAA TAT GTG GGC TTT GTT        336
Lys Asp Ile Gln Arg Ala Tyr Asp Gln Tyr Val Gly Phe Val
100             105                 110

ATA TTA CAT GGT ACT GAT ACA CTG GCA TAT ACG                    369
Ile Leu His Gly Thr Asp Thr Leu Ala Tyr Thr
115             120
```

(2) INFORMATION FOR SEQ ID NO:10:

(i) SEQUENCE CHARACTERISTICS:
        (A) LENGTH: 369 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

```
CGTATATGCC AGTGTATCAG TACCATGTAA TATAACAAAG CCCACATATT          50

GATCGTAAGC TCTTTGAATA TCTTTACCGA TATGAATCCA GTCATCAAAT         100

GTCATATCTG ATGAATCCAA AAGTGGATCA TATTCGATCA TCCAATAAAC         150

AACACGTTTT TTTGAATGTT GTAGTGGTGG CAAACAATAT GGCCTTATTT         200

CGGCGTCAGA ATAATATGTG GACACATAAT CATCATCGTT TAATAGTGAT         250

AAATCACGTA TGGCATGCAG AAGATAATTA GCTTCTGGCT GATACACTCC         300

ATCAATGTAT TTCATCCCAA TCGTTCCACC TGTATATAGC ACTAAAACAT         350

GCGCTTCTTC ACACTGCAT                                           369
```

(2) INFORMATION FOR SEQ ID NO:11:

(i) SEQUENCE CHARACTERISTICS:
        (A) LENGTH: 1770 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1770

(xi) SEQUENCE DESCRIPTION: SEQ ID NO:11:

```
ATG CAG TGT GAA GAA GCG CAT GTT TTA GTG CTA TAT ACA GGT         42
Met Gln Cys Glu Glu Ala His Val Leu Val Leu Tyr Thr Gly
  1               5                  10

GGA ACG ATT GGG ATG AAA TAC ATT GAT GGA GTG TAT CAG CCA         84
Gly Thr Ile Gly Met Lys Tyr Ile Asp Gly Val Tyr Gln Pro
 15              20                  25

GAA GCT AAT TAT CTT CTG CAT GCC ATA CGT GAT TTA TCA CTA        126
Glu Ala Asn Tyr Leu Leu His Ala Ile Arg Asp Leu Ser Leu
 30              35                  40

TTA AAC GAT GAT GAT TAT GTG TCC ACA TAT TAT TCT GAC GCC        168
Leu Asn Asp Asp Asp Tyr Val Ser Thr Tyr Tyr Ser Asp Ala
```

-continued

```
                45                     50                          55

GAA ATA AGG CCA TAT TGT TTG CCA CCA CTA CAA CAT TCA AAA               210
        Glu Ile Arg Pro Tyr Cys Leu Pro Pro Leu Gln His Ser Lys
        60              65                      70

AAA CGT GTT GTT TAT TGG ATG ATC GAA TAT GAT CCA CTT TTG               252
        Lys Arg Val Val Tyr Trp Met Ile Glu Tyr Asp Pro Leu Leu
        75                  80

GAT TCA TCA GAT ATG ACA TTT GAT GAC TGG ATT CAT ATC GGT               294
        Asp Ser Ser Asp Met Thr Phe Asp Asp Trp Ile His Ile Gly
        85                  90                      95

AAA GAT ATT CAA AGA GCT TAC GAT CAA TAT GTG GGC TTT GTT               336
        Lys Asp Ile Gln Arg Ala Tyr Asp Gln Tyr Val Gly Phe Val
        100                 105                     110

ATA TTA CAT GGT ACT GAT ACA CTG GCA TAT ACG GCA TGT GCT               378
        Ile Leu His Gly Thr Asp Thr Leu Ala Tyr Thr Ala Cys Ala
        115                 120                     125

TTG TCA TTT ATG CTG GAG AAC GTA AGA AAA CCC ATT GTT ATT               420
        Leu Ser Phe Met Leu Glu Asn Val Arg Lys Pro Ile Val Ile
        130                 135                     140

ACA GGA GCT CAA ATA CCA GTG TGT GAA GTT CGT TCT GAC GGT               462
        Thr Gly Ala Gln Ile Pro Val Cys Glu Val Arg Ser Asp Gly
        145                 150

CGA GAA AAT TTG ATT GGT GCA CTG ATT ATT GCA GCC AAT TAT               504
        Arg Glu Asn Leu Ile Gly Ala Leu Ile Ile Ala Ala Asn Tyr
        155                 160                     165

GAT ATT CCT GAA GTT ACT GTA TAT TTC AAT AAT AAG CTG TTT               546
        Asp Ile Pro Glu Val Thr Val Tyr Phe Asn Asn Lys Leu Phe
        170                 175                     180

CGA GGA AAT CGT ACA GTA AAA ATA GAT AAC AGA TCA ATG GAT               588
        Arg Gly Asn Arg Thr Val Lys Ile Asp Asn Arg Ser Met Asp
        185                 190                     195

GCT TTT GAA AGT CCA AAT ATG CTT CCA ATT GCT TAC ATG GAT               630
        Ala Phe Glu Ser Pro Asn Met Leu Pro Ile Ala Tyr Met Asp
        200                 205                     210

GTT GAT ATA AAA GTT AAT TAT GAT TCA ATA TTT CGT TCA CCA               672
        Val Asp Ile Lys Val Asn Tyr Asp Ser Ile Phe Arg Ser Pro
        215                 220

TCA ATG GCT CCA TTC GTA GTA CAC GAC CAA TTA TGT CGA AAT               714
        Ser Met Ala Pro Phe Val Val His Asp Gln Leu Cys Arg Asn
        225                 230                     235

GTT GGA TTG TTG AGA ATT TTT CCA TCG ATG TCT ATA GAA AAC               756
        Val Gly Leu Leu Arg Ile Phe Pro Ser Met Ser Ile Glu Asn
        240                 245                     250

GTT AGA GCA TCC TTG CAG GCA CCT ATT GAA GGT GTT GTT CTG               798
        Val Arg Ala Ser Leu Gln Ala Pro Ile Glu Gly Val Val Leu
        255                 260                     265

CAG ACG TTT GGT GCT GGT AAT ATG CCC TCC CAT AGG ACA GAT               840
        Gln Thr Phe Gly Ala Gly Asn Met Pro Ser His Arg Thr Asp
        270                 275                     280

ATA ATC GAT GAA TTG AAA AAA GCT GTT GAT CGA GGA TGT ATT               882
        Ile Ile Asp Glu Leu Lys Lys Ala Val Asp Arg Gly Cys Ile
        285                 290

ATT ATT AAT TGC TCA CAG TGT GTC CGT GGA CAA GTA GAT ATT               924
        Ile Ile Asn Cys Ser Gln Cys Val Arg Gly Gln Val Asp Ile
        295                 300                     305

CAT TAT TTA ACG GGA AAG GTT CTA TAC GAC ATG GGA ATT ATT               966
        His Tyr Leu Thr Gly Lys Val Leu Tyr Asp Met Gly Ile Ile
        310                 315                     320

CCT GGT TCA GAT ATG ACT GCA GAA GCA GCA TTA ACA AAA TTA              1008
```

```
                                                      -continued

Pro Gly Ser Asp Met Thr Ala Glu Ala Ala Leu Thr Lys Leu
325                 330                 335

TCG TAT GTA TTG AGC AAA GAT TGT TGG GAA CTT GTG GAG AAA        1050
Ser Tyr Val Leu Ser Lys Asp Cys Trp Glu Leu Val Glu Lys
340                 345                 350

AAA GCA ATG ATG GTT AAA AAT ATC AGA GGC GAA TTA ACT GTT        1092
Lys Ala Met Met Val Lys Asn Ile Arg Gly Glu Leu Thr Val
355                 360

GCA AAA GCA GAA CCA CTC AAA GAT CTA GAA ATC GTA TCA CAG        1134
Ala Lys Ala Glu Pro Leu Lys Asp Leu Glu Ile Val Ser Gln
365                 370                 375

ATG GCA AGA TTC CTG CAT CTA AGT TCT TCT CAT GAA ATG AAA        1176
Met Ala Arg Phe Leu His Leu Ser Ser Ser His Glu Met Lys
380                 385                 390

CTC CTC TGT CAT GCT ATT TTT CCA CAA TTA TTG TGT TAT GCA        1218
Leu Leu Cys His Ala Ile Phe Pro Gln Leu Leu Cys Tyr Ala
395                 400                 405

GCT AGT AAT GGG GAT ATC GAA ATG CTA AAG GCA CTT CAT GAA        1260
Ala Ser Asn Gly Asp Ile Glu Met Leu Lys Ala Leu His Glu
410                 415                 420

AAT GGA GTT GAT CTT TCG GTT GTT GAC TAT AAT GGA CGC AAT        1302
Asn Gly Val Asp Leu Ser Val Val Asp Tyr Asn Gly Arg Asn
425                 430

GCT TTG CAT GTA GCA GCG AGT GCA GGT CAC GTT GGT GCT GTC        1344
Ala Leu His Val Ala Ala Ser Ala Gly His Val Gly Ala Val
435                 440                 445

AAA TAT CTG TTG ACC CAA GGT GTT AGT TTT CAT CTG AGA GAT        1386
Lys Tyr Leu Leu Thr Gln Gly Val Ser Phe His Leu Arg Asp
450                 455                 460

CAA TGG GAT GAG AAT GCC CTC GTA AGT GCA GTA AAA ATG AAA        1428
Gln Trp Asp Glu Asn Ala Leu Val Ser Ala Val Lys Met Lys
465                 470                 475

AAT AAG ATC TTA ATT GAA ACT TTG CGA TCT GCA GGG GCA CTG        1470
Asn Lys Ile Leu Ile Glu Thr Leu Arg Ser Ala Gly Ala Leu
480                 485                 490

CTT TCC ATA AAT TCA CGC AGA TTA GGT GTT GAA CTA TGT CTA        1512
Leu Ser Ile Asn Ser Arg Arg Leu Gly Val Glu Leu Cys Leu
495                 500

TGT GCC AGC TAT GGC GAC ACG GAA ACA CTG AAT TCT TGG CTT        1554
Cys Ala Ser Tyr Gly Asp Thr Glu Thr Leu Asn Ser Trp Leu
505                 510                 515

GCT GCC GGA GCC GAT ATA AAT CAA CAA GAT TAC AAT GGC GAA        1596
Ala Ala Gly Ala Asp Ile Asn Gln Gln Asp Tyr Asn Gly Glu
520                 525                 530

ACT GCT TTG CAT ATT GCG GTG AAA TCG AGA AAT AAG CAA TTG        1638
Thr Ala Leu His Ile Ala Val Lys Ser Arg Asn Lys Gln Leu
535                 540                 545

GTA CAT TAT TTG CTG GAT AGA GAT GCA GAT CCA TAC AAA ATT        1680
Val His Tyr Leu Leu Asp Arg Asp Ala Asp Pro Tyr Lys Ile
550                 555                 560

GAC GAT TTT AAT TTA ACG CCT CTT AGA CAT GCT AAA AAA CTT        1722
Asp Asp Phe Asn Leu Thr Pro Leu Arg His Ala Lys Lys Leu
565                 570

AAT TTA CAA GAT CTA GTC ATT AGA ATG AAA AAG ATG AAA AAA        1764
Asn Leu Gln Asp Leu Val Ile Arg Met Lys Lys Met Lys Lys
575                 580                 585

GTT CAG                                                        1770
Val Gln
590
```

(2) INFORMATION FOR SEQ ID NO:12:

(i) SEQUENCE CHARACTERISTICS:
        (A) LENGTH: 590 amino acids
        (B) TYPE: amino acid
        (D) TOPOLOGY: linear (ii) MOLECULE TYPE: Protein (xi) SEQUENCE DESCRIPTION: SEQ ID NO:12:

```
Met Gln Cys Glu Glu Ala His Val Leu Val Leu Tyr Thr Gly
  1               5                  10

Gly Thr Ile Gly Met Lys Tyr Ile Asp Gly Val Tyr Gln Pro
 15              20                  25

Glu Ala Asn Tyr Leu Leu His Ala Ile Arg Asp Leu Ser Leu
 30              35                  40

Leu Asn Asp Asp Asp Tyr Val Ser Thr Tyr Tyr Ser Asp Ala
 45                  50                  55

Glu Ile Arg Pro Tyr Cys Leu Pro Pro Leu Gln His Ser Lys
 60              65                  70

Lys Arg Val Val Tyr Trp Met Ile Glu Tyr Asp Pro Leu Leu
 75              80

Asp Ser Ser Asp Met Thr Phe Asp Asp Trp Ile His Ile Gly
 85              90                  95

Lys Asp Ile Gln Arg Ala Tyr Asp Gln Tyr Val Gly Phe Val
100             105                 110

Ile Leu His Gly Thr Asp Thr Leu Ala Tyr Thr Ala Cys Ala
115             120                 125

Leu Ser Phe Met Leu Glu Asn Val Arg Lys Pro Ile Val Ile
130             135                 140

Thr Gly Ala Gln Ile Pro Val Cys Glu Val Arg Ser Asp Gly
145             150

Arg Glu Asn Leu Ile Gly Ala Leu Ile Ile Ala Ala Asn Tyr
155             160                 165

Asp Ile Pro Glu Val Thr Val Tyr Phe Asn Asn Lys Leu Phe
170             175                 180

Arg Gly Asn Arg Thr Val Lys Ile Asp Asn Arg Ser Met Asp
185             190                 195

Ala Phe Glu Ser Pro Asn Met Leu Pro Ile Ala Tyr Met Asp
200             205                 210

Val Asp Ile Lys Val Asn Tyr Asp Ser Ile Phe Arg Ser Pro
215             220

Ser Met Ala Pro Phe Val Val His Asp Gln Leu Cys Arg Asn
225             230                 235

Val Gly Leu Leu Arg Ile Phe Pro Ser Met Ser Ile Glu Asn
240             245                 250

Val Arg Ala Ser Leu Gln Ala Pro Ile Glu Gly Val Val Leu
255             260                 265

Gln Thr Phe Gly Ala Gly Asn Met Pro Ser His Arg Thr Asp
270             275                 280

Ile Ile Asp Glu Leu Lys Lys Ala Val Asp Arg Gly Cys Ile
285             290

Ile Ile Asn Cys Ser Gln Cys Val Arg Gly Gln Val Asp Ile
295             300                 305

His Tyr Leu Thr Gly Lys Val Leu Tyr Asp Met Gly Ile Ile
```

```
310             315             320
Pro Gly Ser Asp Met Thr Ala Glu Ala Ala Leu Thr Lys Leu
325             330             335

Ser Tyr Val Leu Ser Lys Asp Cys Trp Glu Leu Val Glu Lys
340             345             350

Lys Ala Met Met Val Lys Asn Ile Arg Gly Glu Leu Thr Val
355             360

Ala Lys Ala Glu Pro Leu Lys Asp Leu Glu Ile Val Ser Gln
365             370             375

Met Ala Arg Phe Leu His Leu Ser Ser Ser His Glu Met Lys
380             385             390

Leu Leu Cys His Ala Ile Phe Pro Gln Leu Leu Cys Tyr Ala
395             400             405

Ala Ser Asn Gly Asp Ile Glu Met Leu Lys Ala Leu His Glu
410             415             420

Asn Gly Val Asp Leu Ser Val Val Asp Tyr Asn Gly Arg Asn
425             430

Ala Leu His Val Ala Ala Ser Ala Gly His Val Gly Ala Val
435             440             445

Lys Tyr Leu Leu Thr Gln Gly Val Ser Phe His Leu Arg Asp
450             455             460

Gln Trp Asp Glu Asn Ala Leu Val Ser Ala Val Lys Met Lys
465             470             475

Asn Lys Ile Leu Ile Glu Thr Leu Arg Ser Ala Gly Ala Leu
480             485             490

Leu Ser Ile Asn Ser Arg Arg Leu Gly Val Glu Leu Cys Leu
495             500

Cys Ala Ser Tyr Gly Asp Thr Glu Thr Leu Asn Ser Trp Leu
505             510             515

Ala Ala Gly Ala Asp Ile Asn Gln Gln Asp Tyr Asn Gly Glu
520             525             530

Thr Ala Leu His Ile Ala Val Lys Ser Arg Asn Lys Gln Leu
535             540             545

Val His Tyr Leu Leu Asp Arg Asp Ala Asp Pro Tyr Lys Ile
550             555             560

Asp Asp Phe Asn Leu Thr Pro Leu Arg His Ala Lys Lys Leu
565             570

Asn Leu Gln Asp Leu Val Ile Arg Met Lys Lys Met Lys Lys
575             580             585

Val Gln
590
```

(2) INFORMATION FOR SEQ ID NO:13:

(i) SEQUENCE CHARACTERISTICS:
    (A) LENGTH: 1770 nucleotides
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:13:

```
CTGAACTTTT TTCATCTTTT TCATTCTAAT GACTAGATCT TGTAAATTAA          50

GTTTTTTAGC ATGTCTAAGA GGCGTTAAAT TAAAATCGTC AATTTTGTAT         100
```

```
GGATCTGCAT CTCTATCCAG CAAATAATGT ACCAATTGCT TATTTCTCGA         150

TTTCACCGCA ATATGCAAAG CAGTTTCGCC ATTGTAATCT TGTTGATTTA         200

TATCGGCTCC GGCAGCAAGC CAAGAATTCA GTGTTTCCGT GTCGCCATAG         250

CTGGCACATA GACATAGTTC AACACCTAAT CTGCGTGAAT TTATGGAAAG         300

CAGTGCCCCT GCAGATCGCA AAGTTTCAAT TAAGATCTTA TTTTTCATTT         350

TTACTGCACT TACGAGGGCA TTCTCATCCC ATTGATCTCT CAGATGAAAA         400

CTAACACCTT GGGTCAACAG ATATTTGACA GCACCAACGT GACCTGCACT         450

CGCTGCTACA TGCAAAGCAT TGCGTCCATT ATAGTCAACA ACCGAAAGAT         500

CAACTCCATT TTCATGAAGT GCCTTTAGCA TTTCGATATC CCCATTACTA         550

GCTGCATAAC ACAATAATTG TGGAAAAATA GCATGACAGA GGAGTTTCAT         600

TTCATGAGAA GAACTTAGAT GCAGGAATCT TGCCATCTGT GATACGATTT         650

CTAGATCTTT GAGTGGTTCT GCTTTTGCAA CAGTTAATTC GCCTCTGATA         700

TTTTTAACCA TCATTGCTTT TTTCTCCACA AGTTCCCAAC AATCTTTGCT         750

CAATACATAC GATAATTTTG TTAATGCTGC TTCTGCAGTC ATATCTGAAC         800

CAGGAATAAT TCCCATGTCG TATAGAACCT TTCCCGTTAA ATAATGAATA         850

TCTACTTGTC CACGGACACA CTGTGAGCAA TTAATAATAA TACATCCTCG         900

ATCAACAGCT TTTTTCAATT CATCGATTAT ATCTGTCCTA TGGGAGGGCA         950

TATTACCAGC ACCAAACGTC TGCAGAACAA CACCTTCAAT AGGTGCCTGC        1000

AAGGATGCTC TAACGTTTTC TATAGACATC GATGGAAAAA TTCTCAACAA        1050

TCCAACATTT CGACATAATT GGTCGTGTAC TACGAATGGA GCCATTGATG        1100

GTGAACGAAA TATTGAATCA TAATTAACTT TTATATCAAC ATCCATGTAA        1150

GCAATTGGAA GCATATTTGG ACTTTCAAAA GCATCCATTG ATCTGTTATC        1200

TATTTTTACT GTACGATTTC CTCGAAACAG CTTATTATTG AAATATACAG        1250

TAACTTCAGG AATATCATAA TTGGCTGCAA TAATCAGTGC ACCAATCAAA        1300

TTTTCTCGAC CGTCAGAACG AACTTCACAC ACTGGTATTT GAGCTCCTGT        1350

AATAACAATG GGTTTTCTTA CGTTCTCCAG CATAAATGAC AAAGCACATG        1400

CCGTATATGC CAGTGTATCA GTACCATGTA ATATAACAAA GCCCACATAT        1450

TGATCGTAAG CTCTTTGAAT ATCTTTACCG ATATGAATCC AGTCATCAAA        1500

TGTCATATCT GATGAATCCA AAAGTGGATC ATATTCGATC ATCCAATAAA        1550

CAACACGTTT TTTTGAATGT TGTAGTGGTG GCAAACAATA TGGCCTTATT        1600

TCGGCGTCAG AATAATATGT GGACACATAA TCATCATCGT TTAATAGTGA        1650

TAAATCACGT ATGGCATGCA GAAGATAATT AGCTTCTGGC TGATACACTC        1700

CATCAATGTA TTTCATCCCA ATCGTTCCAC CTGTATATAG CACTAAAACA        1750

TGCGCTTCTT CACACTGCAT                                        1770
```

(2) INFORMATION FOR SEQ ID NO:14:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (ii) MOLECULE TYPE: Primer (xi) SEQUENCE DESCRIPTION: SEQ ID NO:14:

AATTAACCCT CACTAAAGGG                                           20

(2) INFORMATION FOR SEQ ID NO:15:

(i) SEQUENCE CHARACTERISTICS:
        (A) LENGTH: 19 nucleotides
        (B) TYPE: nucleic acid
        (C) STRANDEDNESS: single
        (D) TOPOLOGY: linear (ii) MOLECULE TYPE: Primer (xi) SEQUENCE DESCRIPTION: SEQ ID NO:15:

GGAAACAGCT ATGACCATG                                            19

(2) INFORMATION FOR SEQ ID NO:16:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (ii) MOLECULE TYPE: Primer (xi) SEQUENCE DESCRIPTION: SEQ ID NO:16:

CGCTCTAGAA CTAGTGGATC                                           20

(2) INFORMATION FOR SEQ ID NO:17:

(i) SEQUENCE CHARACTERISTICS:
        (A) LENGTH: 22 nucleotides
        (B) TYPE: nucleic acid
        (C) STRANDEDNESS: single
        (D) TOPOLOGY: linear (ii) MOLECULE TYPE:

(xi) SEQUENCE DESCRIPTION: SEQ ID NO:17:

GTAATACGAC TCACTATAGG GC                                        22

(2) INFORMATION FOR SEQ ID NO:18:

(i) SEQUENCE CHARACTERISTICS:
        (A) LENGTH: 17 nucleotides
        (B) TYPE: nucleic acid
        (C) STRANDEDNESS: single
        (D) TOPOLOGY: linear (ii) MOLECULE TYPE: Primer (xi) SEQUENCE DESCRIPTION: SEQ ID NO:18:

GTAAAACGAC GGCCAGT                                              17

(2) INFORMATION FOR SEQ ID NO:19:

(i) SEQUENCE CHARACTERISTICS:
        (A) LENGTH: 25 nucleotides
        (B) TYPE: nucleic acid
        (C) STRANDEDNESS: single
        (D) TOPOLOGY: linear (ii) MOLECULE TYPE: Primer (xi) SEQUENCE DESCRIPTION: SEQ ID NO:19:

CAATATTTCG TTCACCATCA ATGGC                                     25

(2) INFORMATION FOR SEQ ID NO:20:

(i) SEQUENCE CHARACTERISTICS:
        (A) LENGTH: 26 nucleotides
        (B) TYPE: nucleic acid
        (C) STRANDEDNESS: single
        (D) TOPOLOGY: linear (ii) MOLECULE TYPE: Primer (xi) SEQUENCE DESCRIPTION: SEQ ID NO:20:

```
CGGCTCCGGC AGCAAGCCAA GAATTC                                26
```

(2) INFORMATION FOR SEQ ID NO:21:

(i) SEQUENCE CHARACTERISTICS:
        (A) LENGTH: 22 nucleotides
        (B) TYPE: nucleic acid
        (C) STRANDEDNESS: single
        (D) TOPOLOGY: linear (ii) MOLECULE TYPE: Primer (xi) SEQUENCE DESCRIPTION: SEQ ID NO:21:

```
GGTTTAATTA CCCAAGTTTG AG                                    22
```

(2) INFORMATION FOR SEQ ID NO:22:

(i) SEQUENCE CHARACTERISTICS:
        (A) LENGTH: 29 nucleotides
        (B) TYPE: nucleic acid
        (C) STRANDEDNESS: single
        (D) TOPOLOGY: linear (ii) MOLECULE TYPE: Primer (xi) SEQUENCE DESCRIPTION: SEQ ID NO:22:

```
GCCGTATATG CCAGTGTATC AGTACCATG                             29
```

(2) INFORMATION FOR SEQ ID NO:23:

(i) SEQUENCE CHARACTERISTICS:
        (A) LENGTH: 40 nucleotides
        (B) TYPE: nucleic acid
        (C) STRANDEDNESS: single
        (D) TOPOLOGY: linear (ii) MOLECULE TYPE: Primer (xi) SEQUENCE DESCRIPTION: SEQ ID NO:23:

```
CCGAGCTCGA GAATGCAGTG TGAAGAAGCG CATGTTTTAG                 40
```

(2) INFORMATION FOR SEQ ID NO:24:

(i) SEQUENCE CHARACTERISTICS:
        (A) LENGTH: 51 nucleotides
        (B) TYPE: nucleic acid
        (C) STRANDEDNESS: single
        (D) TOPOLOGY: linear (ii) MOLECULE TYPE: Primer (xi) SEQUENCE DESCRIPTION: SEQ ID NO:24:

```
CAGCCAAGCT TCTTACTGAA CTTTTTTCAT CTTTTTCATT CTAATGACTA      50
G                                                           51
```

(2) INFORMATION FOR SEQ ID NO:25:

```
    (i) SEQUENCE CHARACTERISTICS:
         (A) LENGTH: 2073 nucleotides
         (B) TYPE: nucleic acid
         (C) STRANDEDNESS: single
         (D) TOPOLOGY: linear (ii) MOLECULE TYPE: cDNA (ix) FEATURE:
         (A) NAME/KEY: CDS
         (B) LOCATION: 69..1838

(xi) SEQUENCE DESCRIPTION: SEQ ID NO:25:

GGTTTAATTA CCCAAGTTTG AGCAATTAAA TTAGATTGGA AGTATTTATA                    50

CAAATATCAT TCAGTCCG ATG CAG TGT GAA GAA GCG CAT GTT TTA                   95
                    Met Gln Cys Glu Glu Ala His Val Leu
                     1               5

GTG CTA TAT ACA GGT GGA ACG ATT GGG ATG AAA TAC ATT GAT                  137
Val Leu Tyr Thr Gly Gly Thr Ile Gly Met Lys Tyr Ile Asp
 10              15                  20

GGA GTG TAT CAG CCA GAA GCT AAT TAT CTT CTG CAT GCC ATA                  179
Gly Val Tyr Gln Pro Glu Ala Asn Tyr Leu Leu His Ala Ile
 25              30                  35

CGT GAT TTA TCA CTA TTA AAC GAT GAT GAT TAT GTG TCC ACA                  221
Arg Asp Leu Ser Leu Leu Asn Asp Asp Asp Tyr Val Ser Thr
 40              45                  50

TAT TAT TCT GAC GCC GAA ATA AGG CCA TAT TGT TTG CCA CCA                  263
Tyr Tyr Ser Asp Ala Glu Ile Arg Pro Tyr Cys Leu Pro Pro
 55              60                  65

CTA CAA CAT TCA AAA AAA CGT GTT GTT TAT TGG ATG ATC GAA                  305
Leu Gln His Ser Lys Lys Arg Val Val Tyr Trp Met Ile Glu
 70              75

TAT GAT CCA CTT TTG GAT TCA TCA GAT ATG ACA TTT GAT GAC                  347
Tyr Asp Pro Leu Leu Asp Ser Ser Asp Met Thr Phe Asp Asp
 80              85                  90

TGG ATT CAT ATC GGT AAA GAT ATT CAA AGA GCT TAC GAT CAA                  389
Trp Ile His Ile Gly Lys Asp Ile Gln Arg Ala Tyr Asp Gln
 95             100                 105

TAT GTG GGC TTT GTT ATA TTA CAT GGT ACT GAT ACA CTG GCA                  431
Tyr Val Gly Phe Val Ile Leu His Gly Thr Asp Thr Leu Ala
110             115                 120

TAT ACG GCA TGT GCT TTG TCA TTT ATG CTG GAG AAC GTA AGA                  473
Tyr Thr Ala Cys Ala Leu Ser Phe Met Leu Glu Asn Val Arg
125             130                 135

AAA CCC ATT GTT ATT ACA GGA GCT CAA ATA CCA GTG TGT GAA                  515
Lys Pro Ile Val Ile Thr Gly Ala Gln Ile Pro Val Cys Glu
140             145

GTT CGT TCT GAC GGT CGA GAA AAT TTG ATT GGT GCA CTG ATT                  557
Val Arg Ser Asp Gly Arg Glu Asn Leu Ile Gly Ala Leu Ile
150             155                 160

ATT GCA GCC AAT TAT GAT ATT CCT GAA GTT ACT GTA TAT TTC                  599
Ile Ala Ala Asn Tyr Asp Ile Pro Glu Val Thr Val Tyr Phe
165             170                 175

AAT AAT AAG CTG TTT CGA GGA AAT CGT ACA GTA AAA ATA GAT                  641
Asn Asn Lys Leu Phe Arg Gly Asn Arg Thr Val Lys Ile Asp
180             185                 190

AAC AGA TCA ATG GAT GCT TTT GAA AGT CCA AAT ATG CTT CCA                  683
Asn Arg Ser Met Asp Ala Phe Glu Ser Pro Asn Met Leu Pro
195             200                 205

ATT GCT TAC ATG GAT GTT GAT ATA AAA GTT AAT TAT GAT TCA                  725
Ile Ala Tyr Met Asp Val Asp Ile Lys Val Asn Tyr Asp Ser
```

```
                                      -continued 210                215

ATA TTT CGT TCA CCA TCA ATG GCT CCA TTC GTA GTA CAC GAC      767
Ile Phe Arg Ser Pro Ser Met Ala Pro Phe Val Val His Asp
220                225                230

CAA TTA TGT CGA AAT GTT GGA TTG TTG AGA ATT TTT CCA TCG      809
Gln Leu Cys Arg Asn Val Gly Leu Leu Arg Ile Phe Pro Ser
235                240                245

ATG TCT ATA GAA AAC GTT AGA GCA TCC TTG CAG GCA CCT ATT      851
Met Ser Ile Glu Asn Val Arg Ala Ser Leu Gln Ala Pro Ile
250                255                260

GAA GGT GTT GTT CTG CAG ACG TTT GGT GCT GGT AAT ATG CCC      893
Glu Gly Val Val Leu Gln Thr Phe Gly Ala Gly Asn Met Pro
265                270                275

TCC CAT AGG ACA GAT ATA ATC GAT GAA TTG AAA AAA GCT GTT      935
Ser His Arg Thr Asp Ile Ile Asp Glu Leu Lys Lys Ala Val
280                285

GAT CGA GGA TGT ATT ATT ATT AAT TGC TCA CAG TGT GTC CGT      977
Asp Arg Gly Cys Ile Ile Ile Asn Cys Ser Gln Cys Val Arg
290                295                300

GGA CAA GTA GAT ATT CAT TAT TTA ACG GGA AAG GTT CTA TAC     1019
Gly Gln Val Asp Ile His Tyr Leu Thr Gly Lys Val Leu Tyr
305                310                315

GAC ATG GGA ATT ATT CCT GGT TCA GAT ATG ACT GCA GAA GCA     1061
Asp Met Gly Ile Ile Pro Gly Ser Asp Met Thr Ala Glu Ala
320                325                330

GCA TTA ACA AAA TTA TCG TAT GTA TTG AGC AAA GAT TGT TGG     1103
Ala Leu Thr Lys Leu Ser Tyr Val Leu Ser Lys Asp Cys Trp
335                340                345

GAA CTT GTG GAG AAA AAA GCA ATG ATG GTT AAA AAT ATC AGA     1145
Glu Leu Val Glu Lys Lys Ala Met Met Val Lys Asn Ile Arg
350                355

GGC GAA TTA ACT GTT GCA AAA GCA GAA CCA CTC AAA GAT CTA     1187
Gly Glu Leu Thr Val Ala Lys Ala Glu Pro Leu Lys Asp Leu
360                365                370

GAA ATC GTA TCA CAG ATG GCA AGA TTC CTG CAT CTA AGT TCT     1229
Glu Ile Val Ser Gln Met Ala Arg Phe Leu His Leu Ser Ser
375                380                385

TCT CAT GAA ATG AAA CTC CTC TGT CAT GCT ATT TTT CCA CAA     1271
Ser His Glu Met Lys Leu Leu Cys His Ala Ile Phe Pro Gln
390                395                400

TTA TTG TGT TAT GCA GCT AGT AAT GGG GAT ATC GAA ATG CTA     1313
Leu Leu Cys Tyr Ala Ala Ser Asn Gly Asp Ile Glu Met Leu
405                410                415

AAG GCA CTT CAT GAA AAT GGA GTT GAT CTT TCG GTT GTT GAC     1355
Lys Ala Leu His Glu Asn Gly Val Asp Leu Ser Val Val Asp
420                425

TAT AAT GGA CGC AAT GCT TTG CAT GTA GCA GCG AGT GCA GGT     1397
Tyr Asn Gly Arg Asn Ala Leu His Val Ala Ala Ser Ala Gly
430                435                440

CAC GTT GGT GCT GTC AAA TAT CTG TTG ACC CAA GGT GTT AGT     1439
His Val Gly Ala Val Lys Tyr Leu Leu Thr Gln Gly Val Ser
445                450                455

TTT CAT CTG AGA GAT CAA TGG GAT GAG AAT GCC CTC GTA AGT     1481
Phe His Leu Arg Asp Gln Trp Asp Glu Asn Ala Leu Val Ser
460                465                470

GCA GTA AAA ATG AAA AAT AAG ATC TTA ATT GAA ACT TTG CGA     1523
Ala Val Lys Met Lys Asn Lys Ile Leu Ile Glu Thr Leu Arg
475                480                485

TCT GCA GGG GCA CTG CTT TCC ATA AAT TCA CGC AGA TTA GGT     1565
```

```
Ser Ala Gly Ala Leu Leu Ser Ile Asn Ser Arg Arg Leu Gly
490                 495

GTT GAA CTA TGT CTA TGT GCC AGC TAT GGC GAC ACG GAA ACA          1607
Val Glu Leu Cys Leu Cys Ala Ser Tyr Gly Asp Thr Glu Thr
500                 505                 510

CTG AAT TCT TGG CTT GCT GCC GGA GCC GAT ATA AAT CAA CAA          1649
Leu Asn Ser Trp Leu Ala Ala Gly Ala Asp Ile Asn Gln Gln
515                 520                 525

GAT TAC AAT GGC GAA ACT GCT TTG CAT ATT GCG GTG AAA TCG          1691
Asp Tyr Asn Gly Glu Thr Ala Leu His Ile Ala Val Lys Ser
530                 535                 540

AGA AAT AAG CAA TTG GTA CAT TAT TTG CTG GAT AGA GAT GCA          1733
Arg Asn Lys Gln Leu Val His Tyr Leu Leu Asp Arg Asp Ala
545                 550                 555

GAT CCA TAC AAA ATT GAC GAT TTT AAT TTA ACG CCT CTT AGA          1775
Asp Pro Tyr Lys Ile Asp Asp Phe Asn Leu Thr Pro Leu Arg
560                 565

CAT GCT AAA AAA CTT AAT TTA CAA GAT CTA GTC ATT AGA ATG          1817
His Ala Lys Lys Leu Asn Leu Gln Asp Leu Val Ile Arg Met
570                 575                 580

AAA AAG ATG AAA AAA GTT CAG TAA TGTTGCTGCA GAAAATAAAG            1861
Lys Lys Met Lys Lys Val Gln
585                 590

ATCTTATGCA CTCAGAATGT ATTCAGAAGT ATGGTACAAA AGCCTTAAAT            1911

TATGCTAGAT CTTGCATGAT TTCTAGCTTT TTAAATGGTA ATTTTTGTTC            1961

CGTCTTTTTT CGCAAAGACT GATATAATTT AATGAAAAAA AACCTTGTTT            2011

ATTCATCGAT TCCTTTTTTA AACAAAATAG TATTTAATGG CTAAAAAAAA            2061

AAAAAAAAAA AA                                                    2073

(2) INFORMATION FOR SEQ ID NO:26:

(i) SEQUENCE CHARACTERISTICS:
        (A) LENGTH: 2073 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

TTTTTTTTTT TTTTTTTTTT AGCCATTAAA TACTATTTTG TTTAAAAAAG             50

GAATCGATGA ATAAACAAGG TTTTTTTTCA TTAAATTATA TCAGTCTTTG            100

CGAAAAAGA CGGAACAAAA ATTACCATTT AAAAAGCTAG AAATCATGCA             150

AGATCTAGCA TAATTTAAGG CTTTTGTACC ATACTTCTGA ATACATTCTG            200

AGTGCATAAG ATCTTTATTT TCTGCAGCAA CATTACTGAA CTTTTTTCAT            250

CTTTTTCATT CTAATGACTA GATCTTGTAA ATTAAGTTTT TTAGCATGTC            300

TAAGAGGCGT TAAATTAAAA TCGTCAATTT TGTATGGATC TGCATCTCTA            350

TCCAGCAAAT AATGTACCAA TTGCTTATTT CTCGATTTCA CCGCAATATG            400

CAAAGCAGTT TCGCCATTGT AATCTTGTTG ATTTATATCG GCTCCGGCAG            450

CAAGCCAAGA ATTCAGTGTT TCCGTGTCGC CATAGCTGGC ACATAGACAT            500

AGTTCAACAC CTAATCTGCG TGAATTTATG GAAAGCAGTG CCCCTGCAGA            550

TCGCAAAGTT TCAATTAAGA TCTTATTTTT CATTTTTACT GCACTTACGA            600

GGGCATTCTC ATCCCATTGA TCTCTCAGAT GAAAACTAAC ACCTTGGGTC            650
```

```
AACAGATATT TGACAGCACC AACGTGACCT GCACTCGCTG CTACATGCAA          700

AGCATTGCGT CCATTATAGT CAACAACCGA AAGATCAACT CCATTTTCAT          750

GAAGTGCCTT TAGCATTTCG ATATCCCCAT TACTAGCTGC ATAACACAAT          800

AATTGTGGAA AAATAGCATG ACAGAGGAGT TTCATTTCAT GAGAAGAACT          850

TAGATGCAGG AATCTTGCCA TCTGTGATAC GATTTCTAGA TCTTTGAGTG          900

GTTCTGCTTT TGCAACAGTT AATTCGCCTC TGATATTTTT AACCATCATT          950

GCTTTTTTCT CCACAAGTTC CCAACAATCT TTGCTCAATA CATACGATAA         1000

TTTTGTTAAT GCTGCTTCTG CAGTCATATC TGAACCAGGA ATAATTCCCA         1050

TGTCGTATAG AACCTTTCCC GTTAAATAAT GAATATCTAC TTGTCCACGG         1100

ACACACTGTG AGCAATTAAT AATAATACAT CCTCGATCAA CAGCTTTTTT         1150

CAATTCATCG ATTATATCTG TCCTATGGGA GGGCATATTA CCAGCACCAA         1200

ACGTCTGCAG AACAACACCT TCAATAGGTG CCTGCAAGGA TGCTCTAACG         1250

TTTTCTATAG ACATCGATGG AAAAATTCTC AACAATCCAA CATTTCGACA         1300

TAATTGGTCG TGTACTACGA ATGGAGCCAT TGATGGTGAA CGAAATATTG         1350

AATCATAATT AACTTTTATA TCAACATCCA TGTAAGCAAT TGGAAGCATA         1400

TTTGGACTTT CAAAAGCATC CATTGATCTG TTATCTATTT TTACTGTACG         1450

ATTTCCTCGA AACAGCTTAT TATTGAAATA TACAGTAACT TCAGGAATAT         1500

CATAATTGGC TGCAATAATC AGTGCACCAA TCAAATTTTC TCGACCGTCA         1550

GAACGAACTT CACACACTGG TATTTGAGCT CCTGTAATAA CAATGGGTTT         1600

TCTTACGTTC TCCAGCATAA ATGACAAAGC ACATGCCGTA TATGCCAGTG         1650

TATCAGTACC ATGTAATATA ACAAAGCCCA CATATTGATC GTAAGCTCTT         1700

TGAATATCTT TACCGATATG AATCCAGTCA TCAAATGTCA TATCTGATGA         1750

ATCCAAAAGT GGATCATATT CGATCATCCA ATAAACAACA CGTTTTTTTG         1800

AATGTTGTAG TGGTGGCAAA CAATATGGCC TTATTTCGGC GTCAGAATAA         1850

TATGTGGACA CATAATCATC ATCGTTTAAT AGTGATAAAT CACGTATGGC         1900

ATGCAGAAGA TAATTAGCTT CTGGCTGATA CACTCCATCA ATGTATTTCA         1950

TCCCAATCGT TCCACCTGTA TATAGCACTA AAACATGCGC TTCTTCACAC         2000

TGCATCGGAC TGAATGATAT TTGTATAAAT ACTTCCAATC TAATTTAATT         2050

GCTCAAACTT GGGTAATTAA ACC                                      2073
```

PARASITIC HELMINTH ASPARAGINASE PROTEINS, NUCLEIC ACID MOLECULES, AND USES THEREOF

CROSS REFERENCE TO RELATED APPLICATIONS

This application is a divisional of U.S. application Ser. No. 09/140,177, filed Aug. 25, 1998, now U.S. Pat. No. 6,042,825 which is a divisional of U.S. application Ser. No.08/929,501, filed Sep. 15, 1997, which issued as U.S. Pat. No. 5,854,051, each entitled "Parasitic Helminth Asparaginase Proteins, Nucleic Acid Molecules, and Uses Thereof".

FIELD OF THE INVENTION

The present invention relates to parasitic helminth asparaginase nucleic acid molecules, proteins encoded by such nucleic acid molecules, antibodies raised against such proteins, and inhibitors of such proteins. The present invention also includes therapeutic compositions comprising such nucleic acid molecules, proteins, antibodies, inhibitors, and combinations thereof, as well as the use of these compositions to protect animals from diseases caused by parasitic helminths, such as heartworm disease.

BACKGROUND OF THE INVENTION

Parasitic helminth infections in animals, including humans, are typically treated by chemical drugs. One disadvantage with chemical drugs is that they must be administered often. For example, dogs susceptible to heartworm are typically treated monthly. Repeated administration of drugs, however, often leads to the development of resistant helminth strains that no longer respond to treatment. Furthermore, many of the chemical drugs cause harmful side effects in the animals being treated, and as larger doses become required due to the build up of resistance, the side effects become even greater. Moreover, a number of drugs only treat symptoms of a parasitic disease but are unable to prevent infection by the parasitic helminth.

An alternative method to prevent parasitic helminth infection includes administering a vaccine against a parasitic helminth. Although many investigators have tried to develop vaccines based on specific antigens, it is well understood that the ability of an antigen to stimulate antibody production does not necessarily correlate with the ability of the antigen to stimulate an immune response capable of protecting an animal from infection, particularly in the case of parasitic helminths. Although a number of prominent antigens have been identified in several parasitic helminths, there is yet to be a commercially available vaccine developed for,any parasitic helminth.

As an example of the complexity of parasitic helminths, the life cycle of D. immitis, the helminth that causes heartworm disease, includes a variety of life forms, each of which presents different targets, and challenges, for immunization. In a mosquito, D. immitis microfilariae go through two larval stages (L1 and L2) and become mature third stage larvae (L3), which can then be transmitted back to the dog when the mosquito takes a blood meal. In a dog, the L3 molt to the fourth larval stage (L4), and subsequently to the fifth stage, or immature adults. The immature adults migrate to the heart and pulmonary arteries, where they mature to adult heartworms. Adult heartworms are quite large and preferentially inhabit the heart and pulmonary arteries of an animal. Sexually mature adults, after mating, produce microfilariae which traverse capillary beds and circulate in the vascular system of the dog.

In particular, heartworm disease is a major problem in dogs, which typically do not develop immunity, even upon infection (i.e., dogs can become reinfected even after being cured by chemotherapy). In addition, heartworm disease is becoming increasingly widespread in other companion animals, such as cats and ferrets. D. immitis has also been reported to infect humans. There remains a need to identify an efficacious composition that protects animals and humans against diseases caused by parasitic helminths, such as heartworm disease. Preferably, such a composition also protects animals from infection by such helminths.

The parasitic helminth cuticle is a complex extracellular structure which is secreted by an underlying syncytium of hypodermal cells. Recent studies have demonstrated that the cuticle of parasitic helminths is a dynamic structure with important absorptive, secretory, and enzymatic activities, and not merely an inert protective covering as was once believed. See, for example, Lustigman, S. 1993, *Parasitology Today*, 9:8, 294–297. In addition, immunological studies have shown the central importance of cuticular antigens as targets for protective immune responses to parasitic helminths.

Asparaginase amidohydrolases catalyze the hydrolysis of asparagine to aspartic acid and ammonia. See, for example, Moola et al., 1994, *Biochem. J.* 302, 921–927. Studies in systems other than the parasitic helminth indicate that asparaginase is essential for effective hydrolysis of exogenous asparagine and uptake of aspartic acid which cannot otherwise be transported across cell membrane. In yeast, studies have demonstrated that L-asparaginase activity increases in exponentially growing cultures and then decreases as the cells enter the stationary phase. Kim, K. W. and Roon, R. J., 1983, *Biochemistry* 22, 2704–2707. Yeast asparaginase is a highly active cell wall mannan protein and is localized external to the cell membrane and is highly effective in the hydrolysis of exogenous asparagine. *Tetrehymena pyriformis*, a protozoan, cannot transport aspartic acid across its membrane, and L-asparaginase has been shown to be an essential enzyme for aspartic acid-uptake in this species. Tsavdaridis et al., 1991, *Biochemistry International* 24:2, 281–290.

Administration of L-asparaginase in experimental animals and humans leads to regression of certain lymphomas and leukemias, although the exact mechanism by which L-asparaginase kills tumor cells is not clear. See, for example, Moola et al., 1994, *Biochem. J.* 302, 921–927.

SUMMARY OP THE INVENTION

The present invention relates to a novel product and process to protect animals against parasitic helminth infection (e.g., to prevent and/or treat such an infection). The present invention provides parasitic helminth asparaginase proteins and mimetopes thereof; parasitic helminth asparaginase nucleic acid molecules, including those that encode such proteins; antibodies raised against such asparaginase proteins (anti-parasitic helminth asparaginase antibodies); and compounds that inhibit asparaginase activity (i.e, inhibitory compounds or inhibitors).

The present invention also includes methods to obtain parasitic helminth asparaginase proteins, nucleic acid molecules, antibodies and inhibitory compounds. Also included in the present invention are therapeutic compositions comprising such proteins, nucleic acid molecules, antibodies, and inhibitory compounds, as well as use of such therapeutic compositions to protect animals from diseases caused by parasitic helminths.

One embodiment of the present invention is an isolated nucleic acid molecule that hybridizes under stringent hybridization conditions with a Dirofilaria immitis D. immitis) asparaginase gene. Such nucleic acid molecules are referred to as asparaginase nucleic acid molecules. A preferred isolated nucleic acid molecule of this embodiment includes a D. immitis asparaginase nucleic acid molecule. A D. immitis asparaginase nucleic acid molecule preferably includes nucleic acid sequence SEQ ID NO:1, SEQ ID NO:3, SEQ ID NO:4, SEQ ID NO:5, SEQ ID NO:6, SEQ ID NO:8, SEQ ID NO:9, SEQ ID NO:10, SEQ ID NO:11, SEQ ID NO:13, SEQ ID NO:25, or SEQ ID NO:26, or allelic variants of any of these sequences.

Another embodiment of the present invention is an isolated nucleic acid molecule that includes a parasitic helminth asparaginase nucleic acid molecule. A preferred parasitic helminth asparaginase nucleic acid molecule of the present invention preferably includes nucleic acid sequence SEQ ID NO:1, SEQ ID NO:3, SEQ ID NO:4, SEQ ID NO:5, SEQ ID NO:6, SEQ ID NO:8, SEQ ID NO:9, SEQ ID NO: 10, SEQ ID NO:11, SEQ ID NO:13, SEQ ID NO:25, or SEQ ID NO:26, or allelic variants of any of these sequences.

The present invention also relates to recombinant molecules, recombinant viruses and recombinant cells that include an isolated asparaginase nucleic acid molecule of the present invention. Also included are methods to produce such nucleic acid molecules, recombinant molecules, recombinant viruses and recombinant cells.

Another embodiment of the present invention includes a non-native parasitic helminth asparaginase protein encoded by a nucleic acid molecule that hybridizes under stringent hybridization conditions with a parasitic helminth asparaginase gene. A preferred parasitic helminth protein is capable of eliciting an immune response when administered to an animal and/or of having parasitic helminth asparaginase activity. A preferred parasitic helminth asparaginase protein is encoded by a nucleic acid molecule that hybridizes under stringent conditions with a nucleic acid molecule including either SEQ ID NO:1, SEQ ID NO:4, SEQ ID NO:6, SEQ ID NO:9, SEQ ID NO:10, SEQ ID NO:11, or SEQ ID NO:25, or allelic variants of any of these sequences.

Another embodiment of the present invention includes a parasitic helminth asparaginase protein. A preferred asparaginase protein includes a D. immitis asparaginase protein. A preferred D. immitis asparaginase protein comprises amino acid sequence SEQ ID NO:2, SEQ ID NO:7, or SEQ ID NO:12.

The present invention also relates to: mimetopes of parasitic helminth asparaginase proteins; isolated antibodies that selectively bind to parasitic helminth asparaginase proteins or mimetopes thereof; and inhibitors of parasitic helminth asparaginase proteins or mimetopes thereof. Also included are methods, including recombinant methods, to produce proteins, mimetopes, antibodies, and inhibitors of the present invention.

Another embodiment of the present invention is a method to identify a compound capable of inhibiting parasitic helminth asparaginase activity, comprising the steps of: (a) contacting a parasitic helminth asparaginase protein with a putative inhibitory compound under conditions in which, in the absence of the compound, the protein has asparaginase activity; and (b) determining if the putative inhibitory compound inhibits the asparaginase activity. Also included in the present invention is a test kit to identify a compound capable of inhibiting parasitic helminth asparaginase activity. Such a test kit includes a parasitic helminth asparaginase protein having asparaginase activity and a means for determining the extent of inhibition of the asparaginase activity in the presence of a putative inhibitory compound.

Yet another embodiment of the present invention is a therapeutic composition that is capable of protecting an animal from disease caused by a parasitic helminth. Such a therapeutic composition includes one or more of the following protective compounds: an isolated parasitic helminth asparaginase protein or a mimetope thereof; an isolated nucleic acid molecule that hybridizes under stringent hybridization conditions with a Dirofilaria immitis asparaginase gene; an isolated antibody that selectively binds to a parasitic helminth asparaginase protein; or an inhibitor of asparaginase protein activity identified by its ability to inhibit parasitic helminth asparaginase activity. A preferred therapeutic composition of the present invention also includes an excipient, an adjuvant, or a carrier. Preferred asparaginase nucleic acid molecule therapeutic compositions of the present invention include genetic vaccines, recombinant virus vaccines, and recombinant cell vaccines. Also included in the present invention is a method to protect an animal from disease caused by a parasitic helminth, comprising the step of administering to the animal a therapeutic composition of the present invention.

DETAILED DESCRIPTION OF THE INVENTION

The present invention provides for isolated parasitic helminth asparaginase proteins, isolated parasitic helminth asparaginase nucleic acid molecules, isolated antibodies directed against parasitic helminth asparaginase proteins, and other inhibitors of parasitic helminth asparaginase activity. As used herein, the terms isolated parasitic helminth asparaginase proteins, and isolated parasitic helminth asparaginase nucleic acid molecules refers to asparaginase proteins and asparaginase nucleic acid molecules derived from a parasitic helminths and which can be obtained from their natural source, or can be produced using, for example, recombinant nucleic acid technology or chemical synthesis. Also included in the present invention is the use of these proteins, nucleic acid molecules, antibodies and other inhibitors as therapeutic compositions to protect animals from parasitic helminth diseases as well as in other applications, such as those disclosed below.

The present invention is based on the surprising discovery of asparaginase in parasitic helminth cuticle. Parasitic helminth asparaginase proteins and nucleic acid molecules of the present invention have utility because they represent novel targets for anti-parasite vaccines and drugs. The products and processes of the present invention are advantageous because they enable the inhibition of parasite physiological functions that depend on asparaginase activity.

To the inventors' knowledge, the present invention is the first disclosure of a protein or nucleic acid molecule exhibiting significant similarity to known asparaginases or asparaginase genes, respectively, being isolated from a parasitic helminth.

One embodiment of the present invention is an isolated protein comprising a parasitic helminth asparaginase protein. It is to be noted that the term "a" or "an" entity refers to one or more of that entity; for example, a protein refers to one or more proteins or at least one protein. As such, the terms "a" (or "an"), "one or more" and "at least one" can be used interchangeably herein. It is also to be noted that the terms "comprising", "including", and "having" can be used interchangeably. Furthermore, a compound "selected from the group consisting of" refers to one or more of the compounds in the list that follows, including mixtures (i.e., combinations) of two or more of the compounds. According to the present invention, an isolated, or biologically pure, protein, is a protein that has been removed from its natural milieu. The terms "isolated" and "biologically pure" do not necessarily reflect the extent to which the protein has been purified. An isolated protein of the present invention can be obtained from its natural source, can be produced using recombinant DNA technology or can be produced by chemical synthesis. When an isolated protein of the present invention is produced using recombinant DNA technology or produced by chemical synthesis, the protein is referred to herein as either an isolated protein or as a non-native protein.

As used herein, an isolated parasitic helminth asparaginase protein can be a full-length protein or any homolog of such a protein. An isolated protein of the present invention, including a homolog, can be identified in a straight-forward manner by the protein's ability to elicit an immune response against a parasitic helminth asparaginase protein or to catalyze the cleavage of asparagine to aspartic acid and ammonia. Examples of parasitic helminth asparaginase homologs include parasitic helminth asparaginase proteins in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation, or addition of glycerophosphatidyl inositol) so that the homolog includes at least one epitope capable of eliciting an immune response against a parasitic helminth asparaginase protein. That is, when the homolog is administered to an animal as an immunogen, using techniques known to those skilled in the art, the animal will produce an immune response against at least one epitope of a natural parasitic helminth asparaginase protein. As used herein, the term "epitope" refers to the smallest portion of a protein or other antigen capable of selectively binding to the antigen binding site of an antibody or a T-cell receptor. It is well accepted by those skilled in the art that the minimal size of a protein epitope is about four amino acids. The ability of a protein to effect an immune response can be measured using techniques known to those skilled in the art.

Parasitic helminth asparaginase protein homologs can be the result of natural allelic variation or natural mutation. Parasitic helminth asparaginase protein homologs of the present invention can also be produced using techniques known in the art including, but not limited to, direct modifications to the protein or modifications to the gene encoding the protein using, for example, classic or recombinant DNA techniques to effect random or targeted mutagenesis.

An asparaginase protein of the present invention is en coded by a parasitic helminth asparaginase nucleic acid molecule. As used herein, a parasitic helminth asparaginase nucleic acid molecule includes a nucleic acid sequence related to a natural parasitic helminth asparaginase gene, and preferably, to a D. immitis asparaginase gene. As used herein, a parasitic helminth asparaginase gene includes all regions that control production of the parasitic helminth asparaginase protein encoded by the gene (such as, but not limited to, transcription, translation or post-translation control regions) as well as the coding region itself, and any introns or non-translated coding regions. As used herein, a gene that "includes" or "comprises" a nucleic acid sequence may include that sequence in one contiguous array, or may include that sequence as fragmented exons. As used herein, the term "coding region" refers to a continuous linear array of nucleotides that translates into a protein. A full-length coding region is that coding region which is translated into a full-length, i.e., a complete, protein as would be initially translated in its natural milieu, prior to any post-translational modifications.

In one embodiment, a parasitic helminth asparaginase gene of the present invention includes the nucleic acid molecule $nDiAsp_{1753}$, which is herein represented by the nucleic acid sequence SEQ ID NO:1 (the coding strand), as well as the complement of SEQ ID NO:1. The production of $nDiAsp_{1753}$ is disclosed in the Examples. The complement of SEQ ID NO:1 (represented herein by SEQ ID NO:3) refers to the nucleic acid sequence of the strand complementary to the strand having SEQ ID NO:1, which can easily be determined by those skilled in the art. Likewise, a nucleic acid sequence complement of any nucleic acid sequence of the present invention refers to the nucleic acid sequence of the nucleic acid strand that is complementary to (i.e., can form a double helix with) the strand for which the sequence is cited.

In another embodiment, a parasitic helminth asparaginase gene of the present invention includes the nucleic acid sequence SEQ ID NO:6, as well as the complement of SEQ ID NO:6. Nucleic acid sequence SEQ ID NO:6 represents the nucleic acid sequence of the coding strand of the nucleic acid molecule denoted herein as $nDiAsp_{439}$, the production of which is disclosed in the Examples. The complement of SEQ ID NO:6 (represented herein by SEQ ID NO:8) refers to the nucleic acid sequence of the strand complementary to the strand having SEQ ID NO:6.

In another embodiment, a parasitic helminth asparaginase gene of the present invention includes the nucleic acid sequence SEQ ID NO:11, as well as the complement of SEQ ID NO:11. Nucleic acid sequence SEQ ID NO:11 represents the nucleic acid sequence of the coding strand of the nucleic acid molecule denoted herein as $nDiAsp_{1770}$, the production of which is disclosed in the Examples. The complement of SEQ ID NO:11 (represented herein by SEQ ID NO:13) refers to the nucleic acid sequence of the strand complementary to the strand having SEQ ID NO:11.

In another embodiment, a parasitic helminth asparaginase gene of the present invention includes the nucleic acid sequence SEQ ID NO:25, as well as the complement of SEQ ID NO:25. Nucleic acid sequence SEQ ID NO:25 represents the nucleic acid sequence of the coding strand of the nucleic acid molecule denoted herein as $nDiAsp_{2073}$, the production of which is disclosed in the Examples. Nucleic acid molecule $nDiAsp_{2073}$ includes the sequence of the isolated coding strand of the apparent full length cDNA encoding a parasitic helminth asparaginase protein expressed in D. immitis. The complement of SEQ ID NO:25 (represented herein by SEQ ID NO:26) refers to the nucleic acid sequence of the strand complementary to the strand having SEQ ID NO:25.

In another embodiment, a parasitic helminth asparaginase gene can be an allelic variant that includes a similar, but not identical, sequence to SEQ ID NO:1, SEQ ID NO:3, SEQ ID NO:4, SEQ ID NO:5, SEQ ID NO:6, SEQ ID NO:8, SEQ ID NO:9, SEQ ID NO:10, SEQ ID NO:11, SEQ ID NO:13, SEQ ID NO:25, or SEQ ID NO:26, or any other nucleic acid sequence cited herein. For example, an allelic variant of a parasitic helminth asparaginase gene including SEQ ID NO:25 and SEQ ID NO:26 is a gene that occurs at essentially the same locus (or loci) in the genome as the gene including SEQ ID NO:25 and SEQ ID NO:26, but which, due to natural variations caused by, for example, mutation or recombination, has a similar but not identical sequence. Because natural selection typically selects against alterations that affect function, an allelic variant usually encodes a protein having a similar activity or function to that of the protein encoded by the gene to which it is being compared. An allelic variant of a gene or nucleic acid molecule can also comprise alterations in the 5' or 3' untranslated regions of the gene (e.g., in regulatory control regions), or can involve alternative splicing of a nascent transcript, thereby bringing alternative exons into juxtaposition. Allelic variants are well known to those skilled in the art and would be expected to be found naturally occurring within parasitic helminths because the helminth genome is diploid, and sexual reproduction will result in the reassortment of alleles.

In one embodiment of the present invention, isolated asparaginase proteins are encoded by nucleic acid molecules that hybridize under stringent hybridization conditions to a gene encoding a parasitic helminth asparaginase protein (i.e., to a *D. immitis* asparaginase gene). The minimal size of an asparaginase protein of the present invention is a size sufficient to be encoded by a nucleic acid molecule capable of forming a stable hybrid (i.e., hybridize under stringent hybridization conditions) with the complementary sequence of a nucleic acid molecule encoding the corresponding natural protein. As used herein, "stringent hybridization conditions" refer to those experimental conditions under which nucleic acid molecules having similar nucleic acid sequences will anneal to each other. Stringent hybridization conditions, as defined herein, permit the hybridization of nucleic acid molecules having at least about 70% nucleic acid sequence identity with the nucleic acid molecule being used as a probe in the hybridization reaction, i.e., permit the hybridization of a nucleic acid molecule to a probe having up to about 30% base-pair mismatch. Formulae to calculate the appropriate hybridization and wash conditions to achieve hybridization permitting 30% or less mismatch between two nucleic acid molecules are disclosed, for example, in Meinkoth et al, 1984, *Anal Biochem* 138, 267–284; Meinkoth et al, ibid, is incorporated by reference herein in its entirety. The size of a nucleic acid molecule encoding such a protein homolog is dependent on the nucleic acid composition and the percent homology between the nucleic acid molecule and complementary sequence. It should also be noted that the extent of homology required to form a stable hybrid can vary depending on whether the homologous sequences are interspersed throughout a given nucleic acid molecule or are clustered (i.e., localized) in distinct regions on a given nucleic acid molecule. The minimal size of such a nucleic acid molecule is typically at least about 12 to about 15 nucleotides in length if the nucleic acid molecule is GC-rich and at least about 15 to about 17 bases in length if it is AT-rich. As such, the minimal size of a nucleic acid molecule used to encode an asparaginase protein homolog of the present invention is from about 12 to about 18 nucleotides in length. Thus, the minimal size of an asparaginase protein homolog of the present invention is from about 4 to about 6 amino acids in length. There is no limit, other than a practical limit, on the maximal size of such a nucleic acid molecule in that the nucleic acid molecule can include a portion of a gene, an entire gene, or multiple genes. The preferred size of a protein encoded by a nucleic acid molecule of the present invention depends on whether a full-length, fusion, multivalent, or functional portion of such a protein is desired.

One embodiment of the present invention includes a parasitic helminth protein having asparaginase enzyme activity. Such an asparaginase protein preferably includes the ability to catalyze the cleavage of asparagine to aspartic acid and ammonia.

A preferred parasitic helminth asparaginase protein of the present invention is a compound that when administered to an animal in an effective manner, is capable of protecting that animal from disease caused by a parasitic helminth. In accordance with the present invention, the ability of an asparaginase protein of the present invention to protect an animal from disease by a parasitic helminth refers to the ability of that protein to, for example, treat, ameliorate or prevent disease caused by parasitic helminths. In one embodiment, a parasitic helminth asparaginase protein of the present invention can elicit an immune response (including a humoral and/or cellular immune response) against a parasitic helminth.

Suitable parasites to target include any parasite that is essentially incapable of causing disease in an animal administered a parasitic helminth asparaginase protein of the present invention. Accordingly, a parasite to target includes any parasite that produces a protein having one or more epitopes that can be targeted by a humoral or cellular immune response against a parasitic helminth asparaginase protein of the present invention or that can be targeted by a compound that otherwise inhibits parasite asparaginase activity, thereby resulting in the decreased ability of the parasite to cause disease in an animal. Preferred parasites to target include parasitic helminths such as nematodes, cestodes, and trematodes, with nematodes being preferred. Preferred nematodes to target include filariid, ascarid, capillarid, strongylid, strongyloides, trichostrongyle, and trichurid nematodes. Particularly preferred nematodes are those of the genera Acanthocheilonema, Aelurostrongylus, Ancylostoma, Angiostrongylus, Ascaris, Brugia, Bunostomum, Capillaria, Chabertia, Cooperia, Crenosoma, Dictyocaulus, Dioctophyme, Dipetalonema, Diphyllobothrium, Diplydium, Dirofilaria, Dracunculus, Enterobius, Filaroides, Haemonchus, Lagochilascaris, Loa, Mansonella, Muellerius, Nanophyetus, Necator, Nematodirus, Oesophagostomum, Onchocerca, Opisthorchis, Ostertagia, Parafilaria, Paragonimus, Parascaris, Physaloptera, Protostrongylus, Setaria, Spirocerca, Spirometra, Stephanofilaria, Strongyloides, Strongylus, Thelazia, Toxascaris, Toxocara, Trichinella, Trichostrongylus, Trichuris, Uncinaria, and Wuchereria . Preferred filariid nematodes include Dirofilaria, Onchocerca, Acanthocheilonema, Brugia, Dipetalonema, Loa, Parafilaria, Setaria, Stephanofilaria and Wuchereria filariid nematodes, with *D. immitis* being even more preferred.

The present invention also includes mimetopes of parasitic helminth asparaginase proteins of the present invention. As used herein, a mimetope of a parasitic helminth asparaginase protein of the present invention refers to any compound that is able to mimic the activity of a parasitic helminth asparaginase protein (e.g., has the ability to elicit an immune response against a parasitic helminth asparaginase protein of the present invention or ability to inhibit parasitic helminth asparaginase activity). The ability to mimic the activity of a parasitic helminth asparaginase protein is likely to be the result of a structural similarity between the parasitic helminth asparaginase protein and the mimetope. It is to be noted, however, that the mimetope need not have a structure similar to a parasitic helminth asparaginase protein as long as the mimetope functionally mimics the protein. A mimetope can be, but is not limited to: a peptide that has been modified to decrease its susceptibility to degradation (e.g., as an all-D retro peptide); an anti-idiotypic or catalytic antibody, or a fragment thereof; a non-proteinaceous immunogenic portion of an isolated protein (e.g., a carbohydrate structure); or a synthetic or natural organic molecule, including a nucleic acid. Such a mimetope can be designed using computer-generated structures of proteins of the present invention. A mimetope can also be obtained by generating random samples of molecules, such as oligonucleotides, peptides or other organic molecules, and screening such samples by affinity chromatography techniques using the corresponding binding partner.

In one embodiment, a parasitic helminth asparaginase protein of the present invention is a fusion protein that includes a parasitic helminth asparaginase protein-containing domain attached to one or more fusion segments. Suitable fusion segments for use with the present invention include, but are not limited to, segments that can: enhance a protein's stability; act as an inmmunopotentiator to enhance an immune response against a parasitic helminth asparaginase protein; or assist purification of a parasitic helminth asparaginase protein (e.g., by affinity chromatography). A suitable fusion segment can be a domain of any size that has the desired function (e.g., imparts increased stability, imparts increased immunogenicity to a protein, or simplifies purification of a protein). Fusion segments can be joined to the amino or carboxyl termini of a parasitic helminth asparaginase protein-containing domain, and can be susceptible to cleavage in order to enable straight-forward recovery of a parasitic helminth asparaginase protein. A fusion protein is preferably produced by culturing a recombinant cell transformed with a fusion nucleic acid molecule that encodes a protein including a fusion segment attached to either the carboxyl or amino terminal end of an asparaginase protein-containing domain. Preferred fusion segments include a metal binding domain (e.g., a poly-histidine segment); an immunoglobulin binding domain (e.g., Protein A; Protein G; T cell; B cell; Fc receptor or complement protein antibody-binding domains); a sugar binding domain (e.g., a maltose binding domain); and/or a "tag" domain (e.g., at least a portion of β-galactosidase, a strep tag peptide, a T7-tag peptide, a FLAG™ peptide, or other domain that can be purified using compounds that bind to the domain, such as monoclonal antibodies). More preferred fusion segments include metal binding domains, such as a poly-histidine segment; a maltose binding domain; a strep tag peptide, such as that available from Biometra® in Tampa, Fla.; and an S10 peptide. An example of a particularly preferred fusion protein of the present invention is PHIS-PDiAsp$_{509}$, production of which is disclosed herein.

In another embodiment, a parasitic helminth asparaginase protein of the present invention also includes at least one additional protein segment that is capable of protecting an animal from one or more diseases. Such a multivalent protective protein can be produced by culturing a cell transformed with a nucleic acid molecule comprising two or more nucleic acid domains joined together in such a manner that the resulting nucleic acid molecule is expressed as a multivalent protective compound containing at least two protective compounds, or portions thereof, capable of protecting an animal from diseases caused, for example, by at least one infectious agent.

Examples of multivalent protective compounds include, but are not limited to, a parasitic helminth asparaginase protein of the present invention attached to one or more compounds protective against one or more other infectious agents, particularly an agent that infects humans, cats, dogs, ferrets, cattle or horses, such as, but not limited to: viruses (e.g., adenoviruses, caliciviruses, coronaviruses, distemper viruses, hepatitis viruses, herpesviruses, immunodeficiency viruses, infectious peritonitis viruses, leukemia viruses, oncogenic viruses, panleukopenia viruses, papilloma viruses, parainfluenza viruses, parvoviruses, rabies viruses, and reoviruses, as well as other cancer-causing or cancer-related viruses); bacteria (e.g., Actinomyces, Bacillus, Bacterioides, Bordetella, Bartonella, Borrelia, Brucella, Campylobacter, Capnocytophaga, Clostridium, Corynebacterium, Coxiella, Dermatophilus, Enterococcus, Ehrlichia, Escherichia, Francisella, Fusobacterium, Haemobartonella, Helicobacter, Klebsiella, L-form bacteria, Leptospira, Listeria, Mycobacteria, Mycoplasma, Neorickettsia, Nocardia, Pasteurella, Peptococcus, Peptostreptococcus, Proteus, Pseudomonas, Rickettsia, Rochalimaea, Salmonella, Shigelia, Staphylococcus, Streptococcus, and Yersinia; fungi and fungal-related microorganisms (e.g., Absidia, Acremonium, Alternaria, Aspergillus, Basidiobolus, Bipolaris, Blastomyces, Candida, Chlamydia, Coccidioides, Conidiobolus, Cryptococcus, Curvalaria, Epidermophyton, Exophiala, Geotrichum, Histoplasma, Madurella, Malassezia, Microsporum, Moniliella, Mortierella, Mucor, Paecilomyces, Penicillium, Phialemonium, Phialophora, Prototheca, Pseudallescheria, Pseudomicrodochium, Pythium, Rhinosporidium, Rhizopus, Scolecobasidium, Sporothrix, Stemphylium, Trichophyton, Trichosporon, and Xylohypha; and other parasites (e.g., Babesia, Balantidium, Besnoitia, Cryptosporidium, Eimeria, Encephalitozoon, Entamoeba, Giardia, Hammondia, Hepatozoon, Isospora, Leishmania, Microsporidia, Neospora, Nosema, Pentatrichomonas, Plasmodium, Pneumocystis, Sarcocystis, Schistosoma, Theileria, Toxoplasma, and Trypanosoma, as well as helminth parasites, such as those disclosed herein). In one embodiment, a parasitic helminth asparaginase protein of the present invention is attached to one or more additional compounds protective against heartworm disease. In another embodiment, one or more protective compounds, such as those listed above, can be included in a multivalent vaccine comprising a parasitic helminth asparaginase protein of the present invention and one or more other protective molecules as separate compounds.

In one embodiment, a preferred isolated asparaginase protein of the present invention is a protein encoded by a nucleic acid molecule comprising at least a portion of nDiAsp$_{1753}$, nDiAsp$_{1518}$, nDiAsp$_{439}$, nDiAsp$_{369}$, nDiAsp$_{1770}$, or nDiAsp$_{2073}$, or by an allelic variant of any of these nucleic acid molecules. Also preferred is an isolated asparaginase protein encoded by a nucleic acid molecule having the nucleic acid sequence SEQ ID NO:1, SEQ ID NO:4, SEQ ID NO:6, SEQ ID NO:9, SEQ ID NO:11 or SEQ ID NO:25; or by an allelic variant of a nucleic acid molecule having any of these sequences.

Translation of SEQ ID NO:1, the coding strand of nucleic acid molecule nDiAsp$_{1753}$, yields a partial length parasitic helminth asparaginase protein of 506 amino acids, referred to herein as PDiAsp$_{506}$, the amino acid sequence of which is represented by SEQ ID NO:2. The open reading frame spans from nucleotide 1 through nucleotide 1518 of SEQ ID NO:1 and a termination (stop) codon spans from nucleotide 1519 through nucleotide 1521 of SEQ ID NO:1. The coding region encoding PDiAsp$_{506}$, not including the stop codon, is represented by nucleic acid molecule nDiAsp$_{1518}$, having the nucleic acid sequence represented by SEQ ID NO:4 (the coding strand) and SEQ ID NO:5 (the complementary strand). The deduced amino acid sequence SEQ ID NO:2 encodes a protein having a molecular weight of 56.4 kilodaltons (kD) and an estimated pI of about 6.44. The 3' end of the non-coding region of SEQ ID NO:1 has a polyadenylation signal, AATAAA, that spans from nucleotide 1535 to nucleotide 1540, followed by a 20 nucleotide poly-A tail.

Translation of SEQ ID NO:6, the coding strand of nucleic acid molecule nDiAsp$_{439}$, yields a partial length parasitic helminth asparaginase protein of 123 amino acids, referred to herein as PDiAsp$_{123}$, the amino acid sequence of which is represented by SEQ ID NO:7, assuming an open reading frame that spans from nucleotide 69 through nucleotide 71 of SEQ ID NO:6. The coding region encoding PDiAsp$_{123}$ is represented by nucleic acid molecule nDiAsp$_{369}$, having the nucleic acid sequence represented by SEQ ID NO:9 (the coding strand) and SEQ ID NO:10 (the complementary strand). The deduced amino acid sequence SEQ ID NO:7 encodes a protein having a molecular weight of about 14.3 kilodaltons (kD) and an estimated pI of about 4.16.

Translation of SEQ ID NO:11, the coding strand of nucleic acid molecule nDiAsp$_{1770}$, yields an apparent full length parasitic helminth asparaginase protein of 590 amino acids, referred to herein as PDiAsp$_{590}$, the amino acid sequence of which is represented by SEQ ID NO:12, assuming an open reading frame that spans from nucleotide 1 through nucleotide 1770 of SEQ ID NO:11. SEQ ID NO:12 encodes a protein having a molecular weight of about 66,2 kilodaltons (kD) and an estimated pI of about 5.96.

One embodiment of the present invention includes a non-native parasitic helminth asparaginase protein encoded by a nucleic acid molecule that hybridizes under stringent hybridization conditions with a parasitic helminth asparaginase gene. A preferred parasitic helminth protein is capable of eliciting an immune response when administered to an animal and/or of having parasitic helminth asparaginase activity. A preferred parasitic helminth asparaginase protein is encoded by a nucleic acid molecule that hybridizes under stringent conditions with a nucleic acid molecule including either SEQ ID NO: 1, SEQ ID NO:4, SEQ ID NO:6, SEQ ID NO:9, SEQ ID NO:11, or SEQ ID NO:25.

A preferred asparaginase protein of the present invention comprises a protein that is that is at least about 60%, more preferably at least about 65%, more preferably at least about 70%, more preferably at least about 75%, more preferably at least about 80%, more preferably at least about 85%, more preferably at least about 90%, and even more preferably at least about 95% identical to identical to PDiAsp$_{506}$, PDiAsp$_{123}$ or PDiAsp$_{590}$. More preferred is an asparaginase protein comprising PDiAsp$_{506}$, PDiAsp$_{123}$, or PDiAsp590, or a protein encoded by an allelic variant of a nucleic acid molecule encoding a protein comprising PDiAsp$_{506}$, PDiAsp$_{123}$, or PDiAsp$_{590}$.

Also preferred is an asparaginase protein comprising an amino acid sequence that is at least about 60%, more preferably at least about 65%, more preferably at least about 70%, more preferably at least about 75%, more preferably at least about 80%, more preferably at least about 85%, more preferably at least about 90%, and even more preferably at least about 95%, identical to amino acid sequence SEQ ID NO:2, SEQ ID NO:7, or SEQ ID NO:12. Even more preferred is an amino acid sequence having the sequence represented by SEQ ID NO:2, SEQ ED NO:7, or SEQ ID NO:12, or an allelic variant of an amino acid sequence having the sequence represented by SEQ ID NO:2, SEQ ID NO:7, or SEQ ID NO:12.

A particularly preferred parasitic helminth asparaginase protein of the present invention comprises amino acid sequence SEQ ID NO:12, including, but not limited to, an asparaginase protein consisting of amino acid sequence SEQ ID NO:12, a fusion protein or a multivalent protein; or a protein encoded by an allelic variant of a nucleic acid molecule encoding a protein having amino acid sequence SEQ ID NO:12.

Another embodiment of the present invention is an isolated nucleic acid molecule comprising a parasitic helminth asparaginase nucleic acid molecule. The identifying characteristics of such a nucleic acid molecule are heretofore described. A nucleic acid molecule of the present invention can include an isolated natural parasitic helminth asparaginase gene or a homolog thereof, the latter of which is described in more detail below. A nucleic acid molecule of the present invention can include one or more regulatory regions, a full-length or a partial coding region, or a combination thereof. The minimal size of a nucleic acid molecule of the present invention is a size sufficient to allow the formation of a stable hybrid (i.e., hybridization under stringent hybridization conditions) with the complementary sequence of another nucleic acid molecule. Accordingly, the minimal size of an asparaginase nucleic acid molecule of the present invention is from about 12 to about 18 nucleotides in length. A preferred asparaginase nucleic acid molecule includes a parasitic helminth asparaginase nucleic acid molecule.

In accordance with the present invention, an isolated nucleic acid molecule is a nucleic acid molecule that has been removed from its natural milieu (i.e., that has been subject to human manipulation) and can include DNA, RNA, or derivatives of either DNA or RNA. As such, "isolated" does not reflect the extent to which the nucleic acid molecule has been purified. An isolated parasitic helminth asparaginase nucleic acid molecule of the present invention can be isolated from its natural source or produced using recombinant DNA technology (e.g., polymerase chain reaction (PCR) amplification or cloning) or chemical synthesis. Isolated parasitic helminth asparaginase nucleic acid molecules can include, for example, natural allelic variants and nucleic acid molecules modified by nucleotide insertions, deletions, substitutions, or inversions in a manner such that the modifications do not substantially interfere with the nucleic acid molecule's ability to encode an asparaginase protein of the present invention.

A parasitic helminth asparaginase nucleic acid molecule homolog can be produced using a number of methods known to those skilled in the art. See, for example, Sambrook et al., 1989, *Molecular Cloning: A Laboratory Manual*, Cold Spring Harbor Labs Press; Sambrook et al., ibid., is incorporated by reference herein in its entirety. For example, a nucleic acid molecule can be modified using a variety of techniques including, but not limited to, classic mutagenesis and recombinant DNA techniques such as site-directed mutagenesis, chemical treatment, restriction enzyme cleavage, ligation of nucleic acid fragments, PCR amplification, synthesis of oligonucleotide mixtures and ligation of mixture groups to "build" a mixture of nucleic-acid molecules, and combinations thereof. A nucleic acid molecule homolog can be selected by hybridization with a parasitic helminth asparaginase nucleic acid molecule or by screening the function of a protein encoded by the nucleic acid molecule (e.g., ability to elicit an immune response against at least one epitope of a parasitic helminth asparaginase protein, or the ability to demonstrate asparaginase activity).

An isolated nucleic acid molecule of the present invention can include a nucleic acid sequence that encodes a parasitic helminth asparaginase protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a parasitic helminth asparaginase protein.

A preferred nucleic acid molecule of the present invention, when administered to an animal, is capable of protecting that animal from disease caused by a parasitic helminth. As will be disclosed in more detail below, such a nucleic acid molecule can be, or can encode, an antisense RNA, a molecule capable of triple helix formation, a ribozyme, or other nucleic acid-based drug compound. In additional embodiments, a nucleic acid molecule of the present invention can encode a protective protein (e.g., an asparaginase protein of the present invention), the nucleic acid molecule being delivered to the animal, for example, by direct injection (i.e, as a genetic vaccine) or in a vehicle such as a recombinant virus vaccine or a recombinant cell vaccine.

One embodiment of the present invention is an isolated nucleic acid molecule that hybridizes under stringent hybridization conditions with a parasitic helminth asparaginase gene. Preferred parasitic helminth asparaginase genes of the present invention are asparaginase genes from *Dirofilaria immitis*. Such nucleic acid molecules are referred to as parasitic helminth asparaginase nucleic acid molecules. A parasitic helminth asparaginase gene preferably includes at least one of the following nucleic acid sequences: SEQ ID NO:1, SEQ ID NO:3, SEQ ID NO:4, SEQ ID NO:5, SEQ ID NO:6, SEQ ID NO:8, SEQ ID NO:9, SEQ ID NO:10, SEQ ID NO:11, SEQ ID NO:13, SEQ ID NO:25, or SEQ ID NO:26.

In another embodiment, a parasitic helminth asparaginase nucleic acid molecule of the present invention includes a nucleic acid molecule that is at least about 70%, more preferably at least about 75%, more preferably at least about 80%, more preferably at least about 85%, more preferably at least about 90%, and even more preferably at least about 95% identical to nucleic acid molecule $nDiAsp_{1753}$, $nDiAsp_{1518}$, $nDiAsp_{439}$, $nDiAsp_{369}$, $nDiAsp_{1770}$, or $nDiAsp_{2073}$, or an allelic variant of any of these nucleic acid molecules. Also preferred is a parasitic helminth asparaginase nucleic acid molecule comprising a nucleic acid sequence that is that is at least about 70%, more preferably at least about 75%, more preferably at least about 80%, more preferably at least about 85%, more preferably at least about 90%, and even more preferably at least about 95% identical to nucleic acid sequence SEQ ID NO:1, SEQ ID NO:3, SEQ ID NO:4, SEQ ID NO:5, SEQ ID NO:6, SEQ ID NO:8, SEQ ID NO:9, SEQ ID NO:10, SEQ ID NO:11, SEQ ID NO:13, SEQ ID NO:25, or SEQ ID NO:26; or an allelic variant of a nucleic acid molecule having any of these sequences.

Particularly preferred is an asparaginase nucleic acid molecule comprising all or part of nucleic acid molecule $nDiAsp_{1753}$, $nDiAsp_{1518}$, $nDiAsp_{439}$, $nDiAsp_{369}$, $nDiAsp_{1770}$, or $nDiAsp_{2073}$, or an allelic variant of any these nucleic acid molecules. Also particularly preferred is a nucleic acid molecule that includes at least a portion of nucleic acid sequence SEQ ID NO:1, SEQ ID NO:3, SEQ ID NO:4, SEQ ID NO:5, SEQ ID NO:6, SEQ ID NO:8, SEQ ID NO:9, SEQ ID NO:10, SEQ ID NO:11, SEQ ID NO:13, SEQ ID NO:25, or SEQ ID NO:26, or an allelic variant of a nucleic acid molecule having any of these nucleic acid sequences. Such a nucleic acid molecule can include nucleotides in addition to those included in the SEQ ID NOs, such as, but not limited to, nucleotides comprising a full-length gene, or nucleotides comprising a nucleic acid molecule encoding a fusion protein or a nucleic acid molecule encoding a multivalent protective compound.

The present invention also includes a nucleic acid molecule encoding a protein having at least a portion of SEQ ID NO:12, or an allelic variant of a nucleic acid molecule encoding a protein having at least a portion of SEQ ID NO:12. The present invention further includes a nucleic acid molecule that has been modified to accommodate codon usage properties of a cell in which such a nucleic acid molecule is to be expressed.

Knowing the nucleic acid sequences of certain parasitic helminth asparaginase nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain other parasitic helminth asparaginase nucleic acid molecules. Such nucleic acid molecules can be obtained in a variety of ways including screening appropriate expression libraries with antibodies of the present invention; traditional cloning techniques using oligonucleotide probes of the present invention to screen appropriate libraries; and PCR amplification of appropriate libraries or DNA using oligonucleotide primers of the present invention. Preferred libraries to screen or from which to amplify nucleic acid molecules include Dirofilaria L3, L4 or adult cDNA libraries as well as genomic DNA libraries. Similarly, preferred DNA sources from which to amplify nucleic acid molecules include Dirofilaria L3, L4 or adult first-strand cDNA syntheses and genomic DNA. Techniques to clone and amplify genes are disclosed, for example, in Sambrook et al., ibid.

The present invention also includes a nucleic acid molecule that is an oligonucleotide capable of hybridizing, under stringent hybridization conditions, with complementary regions of other, preferably longer, nucleic acid molecules of the present invention such as those comprising parasitic helminth asparaginase nucleic acid molecules; or with complementary regions of other parasitic helminth asparaginase nucleic acid molecules. An oligonucleotide of the present invention can be RNA, DNA, or derivatives of either. The minimum size of such an oligonucleotide is the size required for formation of a stable hybrid between the oligonucleotide and a complementary sequence on another nucleic acid molecule. A preferred oligonucleotide of the present invention has a maximum size of about 100 nucleotides. The present invention includes oligonucleotides that can be used as, for example, probes to identify nucleic acid molecules, primers to produce nucleic acid molecules, or therapeutic reagents to inhibit parasitic helminth asparaginase protein production or activity (e.g., as antisense-, triplex formation-, ribozyme- and/or RNA drug-based reagents). The present invention also includes the use of such oligonucleotides to protect animals from disease using one or more of such technologies. Appropriate oligonucleotide-containing therapeutic compositions can be administered to an animal using techniques known to those skilled in the art.

Another embodiment of the present invention includes a recombinant vector, which includes at least one isolated nucleic acid molecule of the present invention inserted into any vector capable of delivering the nucleic acid molecule into a host cell. Such a vector contains heterologous nucleic acid sequences, that is, nucleic acid sequences that are not naturally found adjacent to nucleic acid molecules of the present invention, and that preferably are derived from a species other than the species from which the nucleic acid molecule(s) are derived. The vector can be either RNA or DNA, either prokaryotic or eukaryotic, and typically is a virus or a plasmid. Recombinant vectors can be used to clone, sequence, or otherwise manipulate a parasitic helminth asparaginase nucleic acid molecule of the present invention.

One type of recombinant vector, referred to herein as a recombinant molecule, comprises a nucleic acid molecule of the present invention operatively linked to an expression vector. The phrase "operatively linked" refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule; Preferably, the expression vector is also capable of replicating within the host cell. An expression vector can be either prokaryotic or eukaryotic, and is typically a virus or a plasmid. An expression vector of the present invention includes any vector that functions (i.e., directs gene expression) in a recombinant cell of the present invention, including in a bacterial, fungal, parasite, insect, other animal, or plant cell. A preferred expression vector of the present invention can direct gene expression in a bacterial, yeast, helminth or other parasite, insect or mammalian cell, or more preferably in a cell type disclosed herein.

In particular, an expression vector of the present invention contains regulatory sequences such as transcription control sequences, translation control sequences, origins of replication, and other regulatory sequences that are compatible with the recombinant cell and that control the expression of a nucleic acid molecule of the present invention. In particular, a recombinant molecule of the present invention includes transcription control sequences. Transcription control sequences are sequences which control the initiation, elongation, and termination of transcription. Particularly important transcription control sequences are those which control transcription initiation, such as promoter, enhancer, operator and repressor sequences. A suitable transcription control sequence includes any transcription control sequence that can function in at least one of the recombinant cells of the present invention. A variety of such transcription control sequences are known to those skilled in the art. Preferred transcription control sequences include those which function in bacterial, yeast, helminth or other parasite, insect or mammalian cells, such as, but not limited to, tac, lac, trp, trc, oxy-pro, omp/lpp, rrnB, bacteriophage lambda (such as lambda $p_L$ and lambda $p_R$ and fusions that include such promoters), bacteriophage T7, T7lac, bacteriophage T3, bacteriophage SP6, bacteriophage SP01, metallothionein, alpha-mating factor, Pichia alcohol oxidase, alphavirus subgenomic promoters (such as Sindbis virus subgenomic promoters), antibiotic resistance gene, baculovirus, Heliothis zea insect virus, vaccinia virus, herpesvirus, raccoon poxvirus, other poxvirus, adenovirus, cytomegalovirus (such as immediate early promoters), picornavirus, simian virus 40, retrovirus, actin, retroviral long terminal repeat, Rous sarcoma virus, heat shock, phosphate or nitrate transcription control sequences; as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with parasitic helminths, such as D immitis or B. malayi.

Suitable and preferred nucleic acid molecules to include in a recombinant vector of the present invention are as disclosed herein. Preferred nucleic acid molecules to include in a recombinant vector, and particularly in a recombinant molecule, include $nDiAsp_{1753}$, $nDiAsp_{1518}$, $nDiAsp_{439}$, $nDiAsp_{369}$, $nDiAsp_{1770}$, and $nDiAsp_{2073}$. A particularly preferred recombinant molecule of the present invention is $PHis-DiAsp_{1770}$, the production of which is described in the Examples section.

A recombinant molecule of the present invention may also (a) contain a secretory signal (i.e., a signal segment nucleic acid sequence) to enable an expressed asparaginase protein of the present invention to be secreted from the cell that produces the protein or (b) contain a fusion sequence which leads to the expression of a nucleic acid molecule of the present invention as a fusion protein. Examples of suitable signal segments include any signal segment capable of directing the secretion of a protein of the present invention. Preferred signal segments include, but are not limited to, native parasitic helminth signal segments, tissue plasminogen activator (t-PA), interferon, interleukin, growth hormone, histocompatibility and viral envelope glycoprotein signal segments. Suitable fusion segments encoded by fusion segment nucleic acids are disclosed herein. In addition, a nucleic acid molecule of the present invention can be joined to a fusion segment that directs the encoded protein to the proteosome, such as a ubiquitin fusion segment. A eukaryotic recombinant molecule may also include intervening and/or untranslated sequences surrounding and/ or within the nucleic acid sequence of the nucleic acid molecule of the present invention.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ, or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a cell include asparaginase nucleic acid molecules disclosed herein. Particularly preferred nucleic acid molecules with which to transform a cell include $nDiAsp_{1753}$, $nDiAsp1518$, $nDiAsp_{439}$, $nDiAsp_{369}$, $nDiAsp_{1770}$, and $nDiAsp_{2073}$.

Suitable host cells to transform include any cell that can be transformed with a nucleic acid molecule of the present invention. Host cells can be either untransformed cells or cells that are already transformed with at least one nucleic acid molecule (e.g., nucleic acid molecules encoding one or more proteins of the present invention or encoding other proteins useful in the production of multivalent vaccines). A recombinant cell of the present invention can be endogenously (i.e., naturally) capable of producing a parasitic helminth asparaginase protein of the present invention or can be capable of producing such a protein after being transformed with at least one nucleic acid molecule of the present invention. A host cell of the present invention can be any cell capable of producing at least one protein of the present invention, and can be a bacterial, fungal (including yeast), parasite (including helminth, protozoa and ectoparasite), other insect, other animal or plant cell. Preferred host cells include bacterial, mycobacterial, yeast, helminth, insect and mammalian cells. More preferred host cells include Salmonella, Escherichia, Bacillus, Listeria, Saccharomyces, Spodoptera, Mycobacteria, Trichoplusia, BHK (baby hamster kidney) cells, MDCK cells (Madin-Darby Canine Kidney cells), CRFK cells (Crandell Feline Kidney cells), BSC-1 cells (African monkey kidney cell line used, for example, to culture poxviruses), COS (e.g., COS-7) cells, and Vero cells. Particularly preferred host cells are *Escherichia coli*, including *E. coli* K-12 derivatives; *Salmonella typhi; Salmonella typhimurium*, including attenuated strains such as UK-1 $\chi$3987 and SR-11 $\chi$4072; *Spodoptera frugiperda; Trichoplusia ni*; BHK cells; MDCK cells; CRFK cells; BSC-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, LMTK$^{31}$ cells and/or HeLa cells. In one embodiment, the proteins may be expressed as heterologous proteins in myeloma cell lines employing immunoglobulin promoters.

A recombinant cell of the present invention includes any cell transformed with at least one of any nucleic acid molecule of the present invention. Suitable and preferred nucleic acid molecules as well as suitable and preferred recombinant molecules with which to transform such a cell are disclosed herein. A particularly preferred recombinant cell is *E. coli*:PHis-DiAsp$_{1770}$.

In one embodiment, a recombinant cell of the present invention can be co-transformed with a recombinant molecule including a parasitic helminth asparaginase nucleic acid molecule encoding a protein of the present invention and a nucleic acid molecule encoding another protective compound, as disclosed herein (e.g., to produce multivalent vaccines).

Recombinant DNA technologies can be used to improve expression of a transformed nucleic acid molecule by manipulating, for example, the number of copies of the nucleic acid molecule within a host cell, the efficiency with which that nucleic acid molecule is transcribed, the efficiency with which the resultant transcript is translated, and the efficiency of post-translational modifications. Recombinant techniques useful for increasing the expression of a nucleic acid molecule of the present invention include, but are not limited to, operatively linking the nucleic acid molecule to a high-copy number plasmid, integration of the nucleic acid molecule into one or more host cell chromosomes, addition of vector stability sequences to a plasmid, substitution or modification of transcription control signals (e.g., promoters, operators, enhancers), substitution or modification of translational control signals (e.g., ribosome binding sites, Shine-Dalgarno sequences, or Kozak sequences), modification of a nucleic acid molecule of the present invention to correspond to the codon usage of the host cell, deletion of sequences that destabilize transcripts, and the use of control signals that temporally separate recombinant cell growth from recombinant enzyme production during fermentation. The activity of an expressed recombinant protein of the present invention may be improved by fragmenting, modifying, or derivatizing a nucleic acid molecule encoding such a protein.

Isolated parasitic helminth asparaginase proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective medium refers to any medium in which a cell is cultured to produce a parasitic helminth asparaginase protein of the present invention. Such a medium typically comprises an aqueous base having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a given recombinant cell. Such culturing conditions are within the expertise of one of ordinary skill in the art. Examples of suitable conditions are included in the Examples section.

Depending on the vector and host system used for production, a resultant protein of the present invention may either remain within the recombinant cell; be secreted into the fermentation medium; be secreted into a space between two cellular membranes, such as the periplasmic space in *E. coli*; or be retained on the outer surface of a cell or viral membrane.

The phrase "recovering the protein", as well as similar phrases, refer to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and preferably should be capable of stimulating the production of antibodies in a treated animal.

The present invention also includes isolated (i.e., removed from their natural milieu) antibodies that selectively bind to a parasitic helminth asparaginase protein of the present invention or a mimetope thereof (e.g., anti-parasitic helminth asparaginase antibodies). As used herein, the term "selectively binds to" an asparaginase protein refers to the ability of an antibody of the present invention to preferentially bind to specified proteins and mimetopes thereof of the present invention. Binding can be measured using a variety of methods standard in the art including enzyme inmmunoassays (e.g., ELISA), immunoblot assays, etc. See, for example, Sambrook et al., ibid., and Harlow, et al., 1988, *Antibodies, a Laboratory Manual*, Cold Spring Harbor Labs Press; Harlow et al., ibid., is incorporated by reference herein in its entirety. An anti-parasitic helminth asparaginase antibody preferably selectively binds to a parasitic helminth asparaginase protein in such a way as to reduce the activity of that protein.

Isolated antibodies of the present invention can include antibodies in serum, or antibodies that have been purified to varying degrees. Antibodies of the present invention can be polyclonal or monoclonal, functional equivalents such as antibody fragments and genetically-engineered antibodies, including single chain antibodies or chimeric antibodies that can bind to more than one epitope.

A preferred method to produce antibodies of the present invention includes (a) administering to an animal an effective amount of a protein, peptide or mimetope thereof of the present invention to produce the antibodies and (b) recovering the antibodies. In another method, antibodies of the present invention are produced recombinantly using techniques as heretofore disclosed to produce asparaginase proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as therapeutic compounds to passively immunize an animal in order to protect the animal from parasitic helminths susceptible to treatment by such antibodies, (b) as reagents in assays to detect infection by such helminths or (c) as tools to screen expression libraries or to recover desired proteins of the present invention from a mixture of proteins and other contaminants. Furthermore, antibodies of the present invention can be used to target cytotoxic agents to parasitic helminths of the present invention in order to directly kill such helminths. Targeting can be accomplished by conjugating (i.e., stably joining) such antibodies to the cytotoxic agents using techniques known to those skilled in the art. Suitable cytotoxic agents are known to those skilled in the art.

One embodiment of the present invention is a therapeutic composition that, when administered to an animal in an effective manner, is capable of protecting that animal from disease caused by a parasitic helminth. A therapeutic composition of the present invention includes an excipient and at least one of the following protective compounds: an isolated native parasitic helminth asparaginase protein; an isolated non-native parasitic helminth asparaginase protein; a mimetope of a parasitic helminth asparaginase protein; an isolated parasitic helminth asparaginase nucleic acid molecule; an isolated antibody that selectively binds to a parasitic helminth asparaginase protein; or an inhibitor of asparaginase protein activity identified by its ability to inhibit parasitic helminth asparaginase activity. As used herein, a protective compound refers to a compound that, when administered to an animal in an effective manner, is able to treat, ameliorate, or prevent disease caused by a parasitic helminth. Preferred helminths to target are heretofore disclosed. Examples of proteins, nucleic acid molecules, antibodies and inhibitors of the present invention are disclosed herein.

The present invention also includes a therapeutic composition comprising at least one parasitic helminth asparaginase-based compound of the present invention in combination with at least one additional compound protective against one or more infectious agents. Examples of such compounds and infectious agents are disclosed herein.

A therapeutic composition of the present invention can be administered to any animal susceptible to such therapy, preferably to mammals, and more preferably to dogs, cats, humans, ferrets, horses, cattle, sheep and other pets, work animals, economic food animals, or zoo animals. Preferred animals to protect against heartworm disease include dogs, cats, humans and ferrets, with dogs and cats being particularly preferred.

In one embodiment, a therapeutic composition of the present invention can be administered to the vector in which the parasitic helminth develops, such as to a mosquito, in order to prevent the spread of parasitic helminth to the definitive mammalian host. Such administration could be orally or by developing transgenic vectors capable of producing at least one therapeutic composition of the present invention. In another embodiment, a vector, such as a mosquito, can ingest therapeutic compositions present in the blood of a host that has been administered a therapeutic composition of the present invention.

A therapeutic composition of the present invention can be formulated in an excipient that the animal to be treated can tolerate. Examples of such excipients include water, saline, Ringer's solution, dextrose solution, Hank's solution, and other aqueous physiologically balanced salt solutions. Non-aqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer, and Tris buffer, while examples of preservatives include thimerosal, —or o-cresol, formalin, and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, a therapeutic composition can include an adjuvant. Adjuvants are agents that are capable of enhancing the immune response of an animal to a specific antigen. Suitable adjuvants include, but are not limited to, cytokines, chemokines, and compounds that induce the production of cytokines and chemokines (e.g., granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL12), interferon gamma, interferon gamma inducing factor I (IGIF), transforming growth factor beta, RANTES (regulated upon activation, normal T-cell expressed and presumably secreted), macrophage inflammatory proteins (e.g., MIP-1 alpha and MIP-1 beta), and Leishmania elongation initiating factor (LEIF)); bacterial components (e.g., endotoxins, in particular superantigens, exotoxins and cell-.wall components); aluminum-based salts; calcium-based salts; silica; polynucleotides; toxoids; serum proteins, viral coat proteins; block copolymer adjuvants (e.g., Hunter's Titermax™ adjuvant (Vaxcel™, Inc. Norcross, Ga.), Ribi adjuvants (Ribi ImmunoChem Research, Inc., Hamilton, Mont.); and saponins and their derivatives (e.g., Quil A (Superfos Biosector A/S, Denmark). Protein adjuvants of the present invention can be delivered in the form of the protein themselves or of nucleic acid molecules encoding such proteins using the methods described herein.

In one embodiment of the present invention, a therapeutic composition can include a carrier. Carriers include compounds that increase the half-life of a therapeutic composition in the treated animal. Suitable carriers include, but are not limited to, polymeric controlled release vehicles, biodegradable implants, liposomes, bacteria, viruses, other cells, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of the treated animal at a constant rate sufficient to attain therapeutic dose levels of the composition to protect an animal from disease caused by parasitic helminths. The therapeutic composition is preferably released over a period of time ranging from about 1 to about 12 months. A controlled release formulation of the present invention is capable of effecting a treatment preferably for at least about I month, more preferably for at least about 3 months, even more preferably for at least about 6 months, even more preferably for at least about 9 months, and even more preferably for at least about 12 months.

In order to protect an animal from disease caused by a parasitic helminth, a therapeutic composition of the present invention is administered to the animal in an effective manner such that the composition is capable of protecting that animal from a disease caused by a parasitic helminth. For example, an isolated protein or mimetope thereof is administered in an amount and manner that elicits (i.e., stimulates) an immune response that is sufficient to protect the animal from the disease. Similarly, an antibody of the present invention, when administered to an animal in an effective manner, is administered in an amount so as to be present in the animal at a titer that is sufficient to protect the animal from the disease, at least temporarily. An oligonucleotide nucleic acid molecule of the present invention can also be administered in an effective manner, thereby reducing expression of native parasitic helminth asparaginase proteins in order to interfere with development of the parasitic helminths targeted in accordance with the present invention.

Therapeutic compositions of the present invention can be administered to animals prior to infection in order to prevent infection (i.e., as a preventative vaccine) or can be administered to animals after infection in order to treat disease caused by the parasitic helminth (i.e., as a curative agent or a therapeutic vaccine).

Acceptable protocols to administer therapeutic compositions in an effective manner include individual dose size, number of doses, frequency of dose administration, and mode of administration. Determination of such protocols can be accomplished by those skilled in the art. A suitable single dose is a dose that is capable of protecting an animal from disease when administered one or more times over a suitable time period. For example, a preferred single dose of a protein, mimetope, or antibody therapeutic composition is from about 1 microgram (μg) to about 10 milligrams (mg) of the therapeutic composition per kilogram body weight of the animal. Booster vaccinations can be administered from about 2 weeks to several years after the original administration. Booster administrations preferably are administered when the immune response of the animal becomes insufficient to protect the animal from disease. A preferred administration schedule is one in which from about 10 μg to about 1 mg of the therapeutic composition per kg body weight of the animal is administered from about one to about two times over a time period of from about 2 weeks to about 12 months. Modes of administration can include, but are not limited to, subcutaneous, intradermal, intravenous, intranasal, oral, transdermal, and intramuscular routes.

According to one embodiment, a nucleic acid molecule of the present invention can be administered to an animal in a fashion to enable expression of that nucleic acid molecule into a protective protein or protective RNA (e.g., an antisense RNA, a ribozyme, a triple helix form, or an RNA drug) in the animal. Nucleic acid molecules can be delivered to an animal by a variety of methods including, but not limited to, (a) administering a genetic vaccine (e.g., a naked DNA or RNA molecule, such as is taught, for example, in Wolff et al., 1990, Science 247, 1465–1468) or (b) administering a nucleic acid molecule packaged as a recombinant virus vaccine or as a recombinant cell vaccine (i.e., the nucleic acid molecule is delivered by a viral or cellular vehicle).

A genetic (i.e., naked nucleic acid) vaccine of the present invention includes a nucleic acid molecule of the present invention and preferably includes a recombinant molecule of the present invention that preferably is replication, or otherwise amplification, competent. A genetic vaccine of the present invention can comprise one or more nucleic acid molecules of the present invention in the form of, for example, a dicistronic recombinant molecule. A preferred genetic vaccine includes at least a portion of a viral genome (i.e., a viral vector). Preferred viral vectors include those based on alphaviruses, poxviruses, adenoviruses, herpesviruses, picornaviruses, and retroviruses, with those based on alphaviruses (such as Sindbis or Semliki forest virus), species-specific herpesviruses and poxviruses being particularly preferred. Any suitable transcription control sequence can be used, including those disclosed as suitable for protein production. Particularly preferred transcription control sequences include cytomegalovirus immediate early (preferably in conjunction with Intron-A), Rous sarcoma virus long terminal repeat, and tissue-specific transcription control sequences, as well as transcription control sequences endogenous to viral vectors if viral vectors are used. The incorporation of "strong" poly(A) sequences is also preferred.

A genetic vaccine of the present invention can be administered in a variety of ways, with intramuscular, subcutaneous, intradermal, transdermal, intranasal and oral routes of administration being preferred. A preferred single dose of a genetic vaccine ranges from about 1 nanogram (ng) to about 500 μg, depending on the route of administration or method of delivery, as can be determined by those skilled in the art. Suitable delivery methods include, for example, by injection, as drops, aerosolized, or topically. Genetic vaccines of the present invention can be contained in an aqueous excipient (e.g., phosphate buffered saline) alone or in a carrier (e.g., lipid-based vehicles).

A recombinant virus vaccine of the present invention includes a recombinant molecule of the present invention that is packaged in a viral coat and that can be expressed in an animal after administration. Preferably, the recombinant molecule is packaging- or replication-deficient or encodes an attenuated virus. A number of recombinant viruses can be used, including, but not limited to, those based on alphaviruses, poxviruses, adenoviruses, herpesviruses, picornaviruses, and retroviruses. Preferred recombinant virus vaccines are those based on alphaviruses (such as Sindbis virus), raccoon poxviruses, picornaviruses, and species-specific herpesviruses. Methods to produce and use a recombinant alphavirus vaccine are disclosed in PCT Publication No. WO 94/17813, by Xiong et al., published Aug. 18, 1994, which is incorporated by reference herein in its entirety.

When administered to an animal, a recombinant virus vaccine of the present invention infects cells within the immunized animal and directs the production of a protective protein or RNA nucleic acid molecule that is capable of protecting the animal from disease caused by a parasitic helminth as disclosed herein. For example, a recombinant virus vaccine comprising a parasitic helminth asparaginase nucleic acid molecule of the present invention is administered according to a protocol that results in the animal producing a sufficient immune response to protect itself from heartworm disease. A preferred single dose of a recombinant virus vaccine of the present invention is from about $1 \times 10^4$ to about $1 \times 10^8$ virus plaque forming units (pfu) per kilogram body weight of the animal. Administration protocols are similar to those described herein for protein-based vaccines, with subcutaneous, intramuscular, intranasal and oral administration routes being preferred.

A recombinant cell vaccine of the present invention includes a recombinant cell of the present invention that expresses at least one protein of the present invention. Preferred recombinant cells for this embodiment include Salmonella, *E. coli*, Listeria, Mycobacterium, *S. frugiperda*, yeast (including *Saccharomyces cerevisiae* and *Pichia pastoris*), BHK, BSC-1, myoblast G8, COS (e.g., COS-7), Vero, MDCK or CRFK recombinant cells. A recombinant cell vaccine of the present invention can be administered in a variety of ways but has the advantage that it can be administered orally, preferably at doses ranging from about $10^8$ to about $10^{12}$ cells per kilogram body weight. Administration protocols are similar to those described herein for protein-based vaccines. A recombinant cell vaccine can comprise whole cells, cells stripped of cell walls or cell lysates.

The efficacy of a therapeutic composition of the present invention to protect an animal from disease caused by a parasitic helminth can be tested in a variety of ways including, but not limited to, detection of protective antibodies (using, for example, proteins or mimetopes of the present invention), detection of cellular immunity within the treated animal, or challenge of the treated animal with the parasitic helminth to determine whether the treated animal is resistant to disease. Challenge studies can include implantation of chambers including parasitic helminth larvae into the treated animal and/or direct administration of larvae to the treated animal. In one embodiment, therapeutic compositions can be tested in animal models such as mice. Such techniques are known to those skilled in the art.

One preferred embodiment of the present invention is the use of parasitic helminth asparaginase proteins, nucleic acid molecules, antibodies or inhibitory compounds of the present invention to protect an animal from heartworm disease. It is particularly preferred to prevent L3 that are delivered to the animal by the mosquito intermediate host from maturing into adult worms. Accordingly, a preferred therapeutic composition is one that is able to inhibit at least one step in the portion of the parasite's development cycle that includes L3, third molt, L4, fourth molt, and immature adult prior to entering the circulatory system. In dogs, this portion of the developmental cycle is about 70 days in length. A particularly preferred therapeutic composition includes a parasitic helminth asparaginase-based therapeutic composition of the present invention, particularly in light of the evidence herein reported that asparaginase is expressed in both larval and adult stages of the parasite. Such a composition can include a parasitic helminth asparaginase nucleic acid molecule, a parasitic helminth asparaginase protein or a mimetope thereof, anti-parasitic helminth asparaginase antibodies, or inhibitors of parasitic helminth asparaginase activity. Such therapeutic compositions are administered to an animal in a manner effective to protect the animals from heartworm disease. Additional protection may be obtained by administering additional protective compounds, including other parasitic helminth proteins, nucleic acid molecules, antibodies and inhibitory compounds, as disclosed herein.

One therapeutic composition of the present invention includes an inhibitor of parasitic helminth asparaginase activity, i.e., a compound capable of substantially interfering with the function of a parasitic helminth asparaginase protein, also referred to herein as an asparaginase inhibitor. In one embodiment, such an inhibitor comprises a compound that interacts directly with an asparaginase protein active site (usually by binding to or modifying the active site), thereby inhibiting asparaginase activity. According to this embodiment, an asparaginase inhibitor can also interact with other regions of an asparaginase protein to inhibit asparaginase activity, for example, by allosteric interaction. Preferably, an asparaginase inhibitor of the present invention is identified by its ability to bind to, or otherwise interact with, a parasitic helminth asparaginase protein, thereby inhibiting asparaginase activity of that protein. Such an asparaginase inhibitor is a suitable for inclusion in a therapeutic composition of the present invention as long as the compound is not harmful to the host animal being treated.

An asparaginase inhibitor can be identified using a parasitic helminth asparaginase protein of the present invention. As such, one embodiment of the present invention is a method to identify a compound capable of inhibiting asparaginase activity of a parasitic helminth susceptible to inhibition by an inhibitor of parasitic helminth asparaginase activity. Such a method includes the steps of (a) contacting (e.g., combining, mixing) an isolated parasitic helminth asparaginase protein, preferably a *D. immitis* asparaginase protein, with a putative inhibitory compound under conditions in which, in the absence of the compound, the protein has asparaginase activity, and (b) determining if the putative inhibitory compound inhibits the asparaginase activity. Putative inhibitory compounds to screen include small organic molecules, antibodies (including mimetopes thereof) and substrate analogs. Methods to determine asparaginase activity are known to those skilled in the art; see, for example, Rhee, et al., ibid., Lim, et al., ibid., Sauri, et al., ibid., and Kim, et al., ibid.

The present invention also includes a test kit to identify a compound capable of inhibiting asparaginase activity of a parasitic helminth. Such a test kit includes an isolated parasitic helminth asparaginase protein, preferably a *D. immitis* asparaginase protein, having asparaginase activity, and a means for determining the extent of inhibition of asparaginase activity in the presence of (i.e., effected by) a putative inhibitory compound. Such compounds are also screened to identify those that are substantially not toxic in host animals, e.g., compounds that do not inhibit the activity of mammalian asparaginase.

Asparaginase inhibitors isolated by such a method or test kit can be used to inhibit any parasitic helminth asparaginase protein that is susceptible to such an inhibitor. A particularly preferred asparaginase inhibitor of the present invention is capable of protecting an animal from heartworm disease. A therapeutic composition comprising a compound that inhibits asparaginase activity can be administered to an animal in an effective manner to protect that animal from disease caused by the parasite expressing the targeted asparaginase enzyme, and preferably to protect that animal from heartworm disease. Effective amounts and dosing regimens can be determined using techniques known to those skilled in the art.

It is also within the scope of the present invention to use isolated proteins, mimetopes, nucleic acid molecules and antibodies of the present invention as diagnostic reagents to detect infection by parasitic helminths. Such diagnostic reagents can be supplemented with additional compounds that can detect specific phases of the parasite's life cycle. Methods to use such diagnostic reagents to diagnose parasitic helminth infection are well known to those skilled in the art. Suitable and preferred parasitic helminths to detect are those to which therapeutic compositions of the present invention are targeted. Particularly preferred parasitic helminths to detect using diagnostic reagents of the present invention are Dirofilaria.

The following examples are provided for the purposes of illustration and are not intended to limit the scope of the present invention.

EXAMPLES

It is to be noted that these Examples include a number of molecular biology, microbiology, immunology and biochemistry techniques familiar to those skilled in the art. Disclosure of such techniques can be found, for example, in Sambrook et al., ibid., Ausubel, et al., 1993, Current Protocols in Molecular Biology, Greene/Wiley Interscience, New York, N.Y., and related references. Ausubel, et al, ibid. is incorporated by reference herein in its entirety. DNA and protein sequence analyses were carried out using the PC/GENE™ sequence analysis program (available from Intelligenetics, Inc., Mountainview, Calif.) and the Wisconsin Package™ Version 9.0 (available from the Genetics Computer Group (GCG), Madison, Wis.). It should also be noted that, because nucleic acid sequencing technology, and in particular the sequencing of PCR products, is not entirely error-free, the nucleic acid and deduced protein sequences presented herein represent apparent nucleic acid sequences of the nucleic acid molecules encoding parasitic helminth asparaginase proteins of the present invention.

Example 1

This Example describes the collection of D. immitis L3 cuticles, preparation of cuticular antigen, and generation of polyclonal antibodies to L3 cuticle.

$L_3$ cuticle collection: Infective stage larvae (L3) collected from mosquitoes were washed three times in NI medium (equal volumes of NCTC-135 and IMDM, available from Sigma Chemical Co., St. Louis, Mo.), then resuspended in NI medium supplemented with 20% SeruMax™ (available from Sigma Chemical Co.). The washed larvae were cultured at a density of 250–440 larvae per ml, with 10 ml per 25 cm$^2$ flask, at 37° C. in an atmosphere of 5% $CO_2$ in air and 95% relative humidity. After culturing in SeruMax-supplemented medium for 48 hr to induce molting, the larvae were washed five times in serum-free medium and then cultured for an additional 4 days. On day 6, the flasks were held at a 45° angle for 20 min to settle the molted L4 larvae. The medium containing the cuticles (which are relatively low density, and therefore float in the culture medium) was then drawn out of the flasks into a 15 ml centrifuge tube. The medium was then spun at 3500 RPM for 15 min to pellet all cuticles. The flasks containing the L4 larvae were resuspended in 5 ml of PBS containing 0.1% Triton X-100, and the above process was repeated two more times to collect cuticles that had settled with the L4 larvae. All cuticle preparations were then pooled and stored at –70° C. until use.

Anti-cuticle antisera: 33,000 L3 cuticles were homogenized in 1 ml of extraction buffer (20 mM Tris/HCl pH 8.5, containing 2 mM 1,4-dithiothreitol, 2 mM EDTA, 1 mM phenylmethylsulfonyl fluoride, 0.1 mM N-tosyl-L-lysine chloromethane and 0.1 mM N-tosyl-L-phenylalanine chloromethane and 0.1% Triton X-100) for 20 min on ice. The crude extract thus obtained was sonicated for three, one min periods, with a five min rest following each minute of sonication, using a pre-chilled small probe of a W-380 Ultrasonic Processor (available from Heat Systems-Ultrasonics, Farmingdale, N.Y.). The cuticle extract was then stored at –70° C. until use.

Twelve mice were immunized subcutaneously, first with approximately 15 μl of larval cuticle extract (approximately 500 larval cuticles) with complete Freund's Adjuvant, and then with three subsequent immunizations of the same dose of extract mixed in incomplete Freund's adjuvant. Immunizations were performed on days 14, 28, 61 and 104. Mice were bled on days 0, 21, 35, 50, 75, 83, 91, 98, 105, 114, 121, 134, and 140, and the cellular blood components were separated from the sera by centrifugation. The sera, referred to herein as anti-cuticle antisera, were stored at –70° C. until use.

An immunoglobulin G- (IgG-) enriched fraction from the anti-cuticle antisera (collected at day 114 post first immunization) was prepared by 50% ammonium sulfate precipitation. This IgG-enriched preparation is referred to herein as IgG-enriched anti-cuticle antisera. Ammonium ions were removed by extensive dialysis in 0.1 M PBS, pH 7.2. The IgG content was determined by measuring absorbance at $OD_{280}$ versus a blank PBS control. IgG from pre-immune mice sera (day 0) was prepared in a similar manner.

Example 2

This Example demonstrates the immunoreactivity (as determined by ELISA) of anti-cuticle antisera.

Total IgG, IgM and IgG subclass antibodies to L3 soluble antigens were measured in sera from mice immunized with L3 cuticles (anti-cuticle antisera, as described above). Crude extracts of D. immitis infective stage larvae (L3) were prepared as follows. Larval heartworm parasites were homogenized in buffer B (20 mM Tris/HCl pH 8.5, containing 2 mM 1,4-dithiothreitol, 2 mM EDTA, 1 mM phenylmethylsulfonyl fluoride, 0.1 mM N-tosyl-L-lysine chloromethane and 0.1 mM N-tosyl-L-phenylalanine chloromethane; all available from Sigma) for 20 min on ice. The crude extracts thus obtained were sonicated continuously for three 1-min periods, with 5-min intervals between each sonication, using a pre-chilled small probe of the W-380 Ultrasonic Processor (available from Heat Systems-Ultrasonics, Farmingdale, N.Y.). The third sonication was done in the presence of 0.1% Triton X-100. The suspensions were centrifuged at 15,000×g for 20 min. The supernatants thus obtained (referred to herein as the parasite extracts, or crude parasite extracts) were diluted to 1.0 μg protein/ml in 0.06 M carbonate buffer, pH 9.6, and then incubated overnight at 4° C. in Immulon®2 microtiter plates (available from Dynatech Laboratories, Alexandria, Va.), 100 μl/well. The plates were blocked with 0.01 M PBS (pH 7.4) containing 0.05% Tween 20 and 5% fetal calf serum (PBS/T/FCS) for 1 hr at 37° C. Serum samples from mice immunized with L3 cuticular antigens (anti-cuticle antisera, prepared as described in Example 1) were diluted 1:25 in PBS/T/FCS and were added to the first row of the ELISA plates. Two-fold dilutions were carried out throughout the remaining rows. After 1 hr incubation at 37° C., the plates were washed with PBS/T, and antibody binding was detected with peroxidase-conjugated anti-mouse total IgG, $IgG_1$, $IgG_{2a}$, $IgG_{2b}$, $IgG_3$ and IgM antibodies, respectively (available from Kirkegaard and Perry Ltd., Gaithersburg, Md.). After 1 hr incubation, the plates were washed and o-phenyldiamine/$H_2O_2$ substrate was added (available from Amresco®, Solon, Ohio). The enzyme reaction was stopped after 5 min at room temperature with 4M $H_2SO_4$. The optical density (OD) was read relative to a PBS blank at 490 nm with an ELISA reader (for example, a SpectraMax® 250, available from Molecular Devices, Sunnyvale, Calif.). A strong total IgG response to L3 soluble antigens in sera from mice immunized with L3 cuticles was observed at day 21 post first immunization. The main IgG subclass that was elevated in these mice was $IgG_1$ isotype. In addition, there was a detectable $IgG_{2b}$ isotype response in these mice to cuticular antigens during the latter part of the immunization schedule (by day 75). Elevated levels of total IgM antibodies were also detected in sera from these mice. [These results are presented in Table 1, which shows the optical density of the wells incubated with a 1:400 dilution of anti-cuticle antisera.]

After centrifugation at 7,000×g for 1 min, 50 larvae per tube were washed once in either PBS (for 0-hr L3 and 48-h L3) or with 0.1% Triton X-100 in PBS for L4 larvae collected 6 days post initial culture. Fifty μl of a 1:4 dilution of IgG-enriched anti-cuticle antisera in PBS was added to the resulting larval pellet and incubated at 4° C. overnight. After three washes as described above, 50 μl of 1:20 dilution of the F(ab)'$_2$ fraction of a fluorescein-conjugated goat anti-mouse IgG (available from Kirkegaard and Perry, Ltd.) was added to the pellet. This preparation was incubated overnight at 4° C., after which the larvae were again washed three times. The resulting larval pellet was resuspended in 50 μl of a 25% glycerol mixture in PBS containing 0.1% p-phenylenediamine. A wet mount of this suspension was placed under a cover slip and observed at 400× using a Model BH-2 Olympus microscope equipped with an exciter IF-490 filter, DM-500 (0–515) dichroic mirror, and a mercury 100 W lamp (available from Olympus Optical Company, Ltd., Tokyo, Japan). A Nikon PI (UFX-11) photometer system equipped with an IF-530 filter and a 2.0 mm diaphragm, was used to quantitate fluorescence (available from Nikon Corporation, Tokyo, Japan). To measure antibody levels to larval surface antigens, three second readings were taken on three representative areas of fluorescence on each of five worms for each serum sample (IgG-enriched anti-cuticle antisera prepared from day 0 and day 114 post immunization), and the highest number within each three second determination was recorded. Data for each serum sample are presented in Table 2 as the average of the fluorescence values of three representative areas on each of five L3 larvae. IgG-enriched anti-cuticle antisera, prepared as described in Example 1, strongly immunoreacted with surface antigens both in 0-hr and 48-hr L3. Pre-immune mouse serum failed to react with larval surface antigens.

TABLE 1

| DAYS POST-INITIAL IMMUIZATION: | 0 | 21 | 35 | 50 | 75 | 83 | 91 | 98 | 105 | 114 | 121 | 134 | 140 |
|---|---|---|---|---|---|---|---|---|---|---|---|---|---|
| ISOTYPE: | | | | | | | | | | | | | |
| total IgG | 0.000 | 0.689 | 2.146 | 2.497 | 3.639 | 3.608 | 3.812 | 3.821 | 3.650 | 4.027 | 3.858 | 3.792 | 3.897 |
| $IgG_1$ | 0.002 | 0.340 | 1.437 | 1.756 | 2.883 | 3.089 | 3.313 | 2.980 | 2.682 | 3.002 | 2.996 | 2.706 | 3.032 |
| $IgG_{2a}$ | 0.007 | 0.030 | 0.107 | 0.119 | 0.229 | 0.211 | 0.279 | 0.218 | 0.190 | 0.221 | 0.200 | 0.193 | 0.213 |
| $IgG_{2b}$ | 0.007 | 0.074 | 0.248 | 0.370 | 0.771 | 0.723 | 0.729 | 0.600 | 0.608 | 0.702 | 0.742 | 0.607 | 0.654 |
| $IgG_3$ | 0.000 | 0.004 | 0.002 | 0.001 | 0.002 | 0.000 | 0.008 | 0.006 | 0.001 | 0.002 | 0.003 | 0.000 | 0.003 |
| IgM | 0.025 | 1.615 | 2.700 | 2.009 | 1.762 | 1.872 | 1.847 | 2.267 | 1.968 | 3.010 | 2.707 | 2.486 | 2.849 |

Example 3

This Example describes quantitation of antibodies to *D. immitis* larval surfaces in sera from mice immunized with L3 cuticles.

Antibodies to larval surfaces in anti-cuticle antisera were quantitated by an indirect fluorescent antibody assay (IFA). Infection of mosquitoes and collection of 0-hr L3 (mosquito-derived infective stage larvae) and 48-hr L3 (48-hr after in vitro culture) were carried out as previously described (Frank, G. R. and Grieve, R. B., 1991, *J Parasitol*77, 950–956). Each larval stage was processed separately. Larvae were fixed for 24 hr at 4° C. in 4% formalin in PBS.

TABLE 2

Reactivity* of IgG-enriched anti-cuticle antisera to *D. immitis* larval surface antigens

| | Relative fluorescence units[†] | |
|---|---|---|
| Larval stage | Mouse pre-bleed IgG | Mouse anti-cuticle IgG |
| 0-hr L3 | 1.1 ± 0.1 | 33.3 ± 3.6 |
| 48-hr L3 | 1.7 ± 0.2 | 13.1 ± 13.2 |

TABLE 2-continued

Reactivity* of IgG-enriched anti-cuticle antisera to *D. immitis* larval surface antigens

| | Relative fluorescence units[†] | |
|---|---|---|
| Larval stage | Mouse pre-bleed IgG | Mouse anti-cuticle IgG |

*Reactivity of IgG-enriched anti-cuticle antisera to *D. immitis* larval surface antigens was measured by indirect fluorescent antibody assay as described in the text.
[†]Data represent Mean ± SD of at least 3 readings per larva (n = 5)

Example 4

This Example describes the isolation and sequencing of *D. immitis* asparaginase (DiASNase) nucleic acid molecules of present invention.

A DiASNase nucleic acid molecule of 1753 nucleotides, herein referred to as nDiASNase$_{1753}$, was cloned from a *D. immitis* larval cDNA library by immunoscreening. Specifically, a *D. immitis* 48-hr L3 cDNA expression library was constructed in Uni-ZAP™ XR vector (available from Stratagene Cloning Systems, La Jolla, Calif.), using a ZAP-cDNA Synthesis Kit (available from Stratagene) and 48-hr L4 mRNAs. The library was immunoscreened using the IgG-enriched anti-cuticle antisera described in Example 1, and standard immunoscreening procedures as described, for example, in Sambrook et al., ibid. Briefly, phage were plated onto a lawn of *E. coli* XL1-Blue MRF' (available from Stratagene) at a density of 25×10$^3$ phage per petri dish (150 mm$^2$) and grown at 37° C. for 4 hr. When plaques were visible, isopropyl-β-D thiogalactoside (IPTG)-impregnated nitrocellulose filters were placed on the plates for 3 hr at 37° C. The filters were then removed and washed in 0.01% M phosphate-buffered saline, pH 7.4 with 0.05% Tween 20 (PBS/T), and then blocked in PBS/T containing 5% nonfat dry milk for one hr at room temperature. The filters were then incubated for 3 hr in mouse IgG-enriched anti-cuticle antisera, diluted 1:200 in PBS/T, that had been previously absorbed with *E. coli* antigens. Antibody reactivity with recombinant proteins was revealed by incubation of the filters with alkaline phosphatase-conjugated goat anti-mouse IgG antibodies (available from Kirkegaard and Perry) for 1 hr, followed by development with 5-bromo-4-chloro-3-indolyl phosphate/nitroblue tetrazolium (BCIP/NBT, available from Sigma). Clones that were reactive with the sera were selected and purified by repeated cycles of immune selection.

The nucleic acid molecule nDiASNase$_{1753}$ included in the plaque-purified cloned DNA was converted into a double stranded recombinant molecule, herein denoted as pβgal-nDiASNase$_{1753}$, using ExAssist™ helper phage and SOLR™ *E. coli* (available from Stratagene) according to the manufacturer's protocol for in vivo excision of DNA. Double stranded plasmid DNA was prepared using an alkaline lysis protocol, such as that described in Sambrook et al., ibid. Due to an internal EcoRI restriction site in nDiASNase$_{1753}$, digestion of the plasmid DNA with EcoRI and XhoI restriction endonucleases resulted in the release of two DiASNase nucleic acid molecules of 463 bp and 1290 bp, namely nDiASNase$_{463}$ and nDiASNase$_{1290}$. These two nucleic acid molecules together make a DiASNase nucleic acid molecule of 1753 nucleotides in size, herein referred to as nDiASNase$_{1753}$.

The plasmid containing nDiASNase$_{1753}$ was sequenced by the Sanger dideoxy chain termination method, using the PRISM™ Ready Dye Terminator Cycle Sequencing Kit with AmpliTaq® DNA Polymerase, FS (available from the Perkin-Elmer Corporation, Norwalk, Conn.). PCR extensions were done in the GeneAmp™ PCR System 9600 (available from Perkin-Elmer). Excess dye terminators were removed from extension products using the Centriflex™ Gel Filtration Cartridge (available from Advanced Genetics Technologies Corporation (ABI), Gaithersburg, Md.) following the manufacturer's protocol. Samples were resuspended according to ABI protocols and then run on a Perkin-Elmer-ABI PRISM™ 377 Automated DNA Sequencer. The following nucleotide primers were used to sequence nDiASNase$_{1753}$: Three pBluescript™ vector sense primers consisting of a) a T$_3$X primer (denoted herein as SEQ ID NO:14) having the nucleic acid sequence, 5' AAT-TAACCCTCACTAAAGGG 3'; b) a M13 reverse primer (denoted herein as SEQ ID NO:15) having the nucleotide sequence, 5' GGAAACAGCTATGACCATG 3'; and c) an SK primer (denoted herein as SEQ ID NO:16) having the nucleotide sequence 5' CGCTCTAGAACTAGTGGATC 3'. In addition, two pBluescript™ vector antisense primers were used, consisting of a T$_7$X primer (denoted herein as SEQ ID NO:17) having the nucleotide sequence 5' GTAATACGACTCACTATAGGGC 3' and a M13 forward primer (denoted herein a SEQ ID NO:18) having the nucleotide sequence 5' GTAAAACGACGGCCAGT 3'. In addition, two nDiASNase$_{1753}$-specific primers derived from the initial partial sequencing of nDiASNase$_{1753}$ were used. These included a sense primer (denoted herein as SEQ ID NO:19) having the nucleotide sequence 5' CAATATTTCGT-TCACCATCAATGGC 3', and an antisense primer (denoted herein as SEQ ID NO:20) having the nucleotide sequence 5' CGGCTCCGGCAGCAAGCCAAGAATTC 3'. These two nDiASNase$_{1753}$-specific primers correspond to the following regions of the coding strand of nDiASNase$_{1753}$ (herein represented by SEQ ID NO:25 (coding strand)): SEQ ID NO:19 corresponds to a region of SEQ ID NO:25 that spans from nucleotide 724 to nucleotide 748, and SEQ ID NO:20 corresponds to a region of SEQ ID NO:25 spanning from nucleotide 1610 to nucleotide 1630. The resulting nucleic acid sequences of the two complementary DNA strands of nDiASNase$_{1753}$ are referred to herein as SEQ ID NO:1 (the coding strand) and SEQ ID NO:3 (the reverse complement of the coding strand).

Translation of SEQ ID NO:1 yields a protein of 506 amino acids, herein denoted PDiASNase$_{506}$, the amino acid sequence of which is represented by SEQ ID NO:2. The nucleic acid molecule encoding PDiASNase$_{506}$ is referred to herein as nDiASNase$_{1518}$, the nucleic acid sequence of which is represented by SEQ ID NO:4 (the coding strand) and the SEQ ID NO:5 (the complementary strand), assuming that the first codon spans from nucleotide 1 through nucleotide 3, and a putative stop codon spans from nucleotide 1519 to nucleotide 1521 (of SEQ ID NO:1). The 3' end of the non-coding region of SEQ ID NO:1 has a polyadenylation signal, AATAAA, spanning from nucleotide 1535 to nucleotide 1540, followed by a 20 nucleotide poly-A tail., The amino acid sequence of PDiASNase$_{506}$ (i.e., SEQ ID NO:2) was analyzed using the PC/GENE (available from Intelligenetics, Inc., Mountain view, Calif.) sequence analysis program. The protein represented by this amino acid sequence has a predicted molecular mass of 56.4 kD and an estimated pI of 6.44. Analysis of PDiASNase$_{506}$ using the method of Hopp and Woods (Hopp and Woods, *Proc. Natl. Acad. Sci.* (*USA*)., 78, 3824–3828) predicts that this protein is hydrophilic.

A homology search of a non-redundant protein database was performed on SEQ ID NO:2 using the BLASTp sequence analysis program available through the BLAST™ network through the National Center for Biotechnology Information (NCBI) (National Library of Medicine, National Institute of Health, Baltimore, Md.). This database includes SwissProt+PIR+SPupdate+GenPept+GPUpdate+ PDB databases. The highest scoring match of the homology search at the amino acid level was to the translation product of a *Caenorhabditis elegans* gene (C27A7.5A), GenBank™ accession number E293495. SEQ ID NO:2 was optimally aligned with the sequence represented by GenBank™ accession number E293495 using the "ALIGN" program available in the PC/GENE™ Package. The alignment revealed that a region spanning from amino acid 1 through amino acid 499 of SEQ ID NO:2 had about 54% identity to a region that spans from amino acid number 1 through amino acid 686 of the translation product of the *C. elegans* cosmid clone.

A BLASTn search of a non-redundant nucleotide database was performed using SEQ ID NO: 1. At the nucleotide level, the coding region represented in SEQ ID NO:1 showed some homology to the *C. elegans* cosmid clone (C27A7.5A) nucleotide sequence, GenBank™ Accession No. Z81041. Optimal alignment using the "ALIGN" program available in the PC/GENE™ Package revealed that a region of SEQ ID NO:1, that spans from nucleotide 1 through nucleotide 1753, had about 65% identity with the nucleotide sequence of Z81041.

Example 5

This Example describes the PCR amplification and subsequent isolation of DiASNase nucleic acid molecules from *D. immitis* larval and adult female first strand cDNA using a primer derived from the sequence of the nematode 22 nucleotide splice leader.

Most, but not all nematode messenger RNAs have the nematode splice leader sequence (SL1) at their 5' ends, and the presence of the 5' SL1 sequence is indicative of an apparent full length cDNA. See, for example Blaxter and Liu, 1996, *Int. J. Parasitol.* 26, 1025–1033, which is incorporated herein by reference. DiASNase nucleic acid molecules were PCR amplified from larval and adult female first strand cDNA using a sense primer representing the nematode splice leader sequence (SL1) having the nucleotide sequence, 5' GGTTTAATTACCCAAGTTTGAG 3' (denoted here in as SEQ ID NO:21). In addition, an anti-sense primer, referred to herein as ASP5'INT (represented by SEQ ID NO:22) and having the nucleotide sequence 5'GCCGTATATGCCAGTGTATCAGTACCATG 3', was used in the amplification reaction. ASP5'INT corresponds to a region of SEQ ID NO:25 that spans from nucleotide 411 through nucleotide 439. PCR amplification of larval and adult female cDNAs yielded identical 439-bp products from both larval and adult first strand cDNAs. The product amplified from adult female cDNA is referred to herein as nDiASNase$_{439}$.

Nucleic acid molecule nDiASNase$_{439}$ was gel purified, cloned into the pCR®2.1 cloning vector (available from Invitrogen, Carlsbad, Calif.) and sequenced as previously described. Sequence analysis demonstrated the presence of the SL1 sequence at the 5' end of nDiASNase$_{439}$. The coding and complementary strands of nDiASNase$_{439}$ are herein denoted as SEQ ID NO:6 and SEQ ID NO:8, respectively. Assuming an initiation codon that spans from nucleotide 69 to nucleotide 71, translation of SEQ ID NO:6 yields a protein of 123 amino acids, herein referred to as PDiASNase$_{123}$, the amino acid sequence of which is represented by SEQ ID NO:7. The coding region of PDiAS-Nase$_{123}$ is referred to herein as nDiASNase$_{369}$, the nucleic acid sequence of which is represented in SEQ ID NO:9 (the coding strand) and SEQ ID NO:10 (the complementary strand). Analysis of the amino acid sequence of *D. immitis* PDiASNase$_{123}$ (i.e., SEQ ID NO:7) predicts that PDiAS-Nase$_{123}$ has an estimated molecular weight of about 14.3 kD and an estimated pI of about 4.16. The fact that nucleic acid molecule nDiASNase$_{439}$ could be amplified from the larval cDNA with the SL1 primer demonstrates that the larval messenger RNA from which nDiASNase$_{1753}$ was amplified had the 5' SL1 sequence.

A homology search of a non-redundant protein database was performed on SEQ ID NO:6 using the BLAST™ network through the National Center for Biotechnology Information (NCBI) (National Library of Medicine, National Institute of Health, Baltimore, Md.). This database includes SwissProt+PIR+SPupdate+GenPept+GPUpdate+ PDB databases. The highest scoring match of the homology search at the amino acid level was to the translation product of the nucleic acid sequence of a *C. elegans* cosmid, GenBank™ accession number E293495. This homology spans from amino acid 1 through amino acid 123 of SEQ ID NO:7. Using this analysis program, the coding region represented in SEQ ID NO:6 from nucleotide 1 to nucleotide 439 was approximately 60% homologous to the sequence of a *C. elegans* cosmid, GenBank™ accession number Z81041.

A composite nucleic acid molecule representing an apparent full-length *D. immitis* asparaginase cDNA molecule was assembled by joining the overlapping nucleic acid sequences of nucleic acid molecules nDiASNase$_{1753}$ and nDiAS-Nase$_{439}$. This composite nucleic acid molecule is denoted herein as nDiASNase$_{2073}$, and has a nucleic acid sequence as represented by SEQ ID NO:25 (the coding strand) and SEQ ID NO:26 (the complementary strand). nDiASNase$_{2073}$ encodes a protein having an amino acid sequence herein represented by SEQ ID NO:12. This protein 3 predicted N-glycosylation sites at amino acid positions 185, 192, and 297 of SEQ ID NO:12. In addition, nDiASNase$_{2073}$ encodes an asparaginase/glutaminase signature sequence spanning from amino acid 10 to amino acid 18 of SEQ ID NO:12.

Example 6

This Example describes the amplification and subsequent isolation of an asparaginase nucleic acid molecule from *D. immitis* female adult cDNA using primers designed for protein expression in pTrcHisB vector. This Example further discloses the production of a recombinant molecule and a recombinant cell of the present invention.

A DiASNase nucleic acid molecule was PCR amplified from female adult cDNA using a sense primer (DiASNase-XhoI) with the sequence, 5' CCbAGCTCGAGAATGCAGT-GTGAAGAAGCGCATGTTTAG 3' (denoted herein as SEQ ID NO:23; XhoI site in bold) corresponding to a region of SEQ ID NO:25 spanning from nucleotide 69 through nucleotide 96, and including a linker sequence not found in SEQ ID NO:25. Also used was an antisense primer (DiASNase-HindIII) 5' CAGCCAAGCTTCTTACT-GAACTTTTTTCATCTTTTTCATTCTAATGACTAG 3' (denoted herein as SEQ ID NO:24; HindIII site in bold) corresponding to a region of SEQ ID NO:25 spanning from nucleotide 1803 through nucleotide 1841, and also including a linker sequence not found in SEQ ID NO:25. PCR amplification of adult female cDNA with these primers yielded a 1770 bp product referred to herein as nDiAS-Nase$_{1770}$.

Nucleic acid molecule nDiASNase$_{1770}$ was gel purified, cloned into a TA cloning vector (available from Invitrogen)

and sequenced using an automated DNA sequencer. The sequence of the coding and complementary strands of nDiASNase$_{1770}$ are herein represented by SEQ ID NO:11 and SEQ ID NO:13, respectively. Translation of SEQ ID NO:11 yields a protein of 590 amino acids, herein denoted PDiASNase$_{590}$, the amino acid sequence of which is presented in SEQ ID NO:12. Analysis of the amino acid sequence of *D. immitis* PDiASNase$_{590}$ (i.e., SEQ ID NO:12) predicts that PDiASNase$_{590}$ has an estimated molecular weight of about 66.2 kD and an estimated pI of about 5.96. The amino acid sequence of PDiASNase$_{590}$ has three potential N-glycosylation sites at positions 185, 192 and 297 of SEQ ID NO:12. In addition, there is an apparent asparaginase/glutaminase signature sequence found at residues 10–18 of SEQ ID NO:11.

Recombinant molecule PTrc-nDiASNase$_{1770}$, containing from nucleotide 1 through nucleotide 1770 of nDiASNase$_{1770}$, operatively linked to trc transcription control sequences and to a fusion sequence encoding a polyhistidine segment comprising 6 histidine residues, was produced in the following manner. Nucleic acid molecule nDiASNase$_{1770}$ (containing nucleotides spanning from nucleotide 1 through nucleotide 1770 of SEQ ID NO:11) was PCR amplified as described above (using a sense primer (DiASNase-XhoI; SEQ ID NO:23) and an antisense primer (DiASNase-HindIII; SEQ ID NO:24). Recombinant molecule PTrc-nDiASNase$_{1770}$ was produced by digesting nDiASNase$_{1770}$ with XhoI and HindIII restriction endonucleases, gel purifying the resulting fragment, and directionally subcloning the fragment into expression vector pTrcHisB (available from Invitrogen) that had been cleaved with XhoI and HindIII.

Recombinant molecule PTrc-nDiASNase$_{1770}$ was transformed into *E. coli*, using standard techniques as disclosed in Sambrook et al., ibid., to form recombinant cell *E. coli*:PTrc-nDiASNase$_{1770}$.

Example 7

This Example describes the production of a DiASNase protein of the present invention in a prokaryotic cell, as well as studies to characterize that protein.

Recombinant cell *E. coli*:PTrc-nDiASNase$_{1770}$, produced as described in Example 5, was cultured in shake-flasks containing an enriched bacterial growth medium and 0.1 mg/ml ampicillin at about 37° C. When the cells reached an OD$_{600}$ of about 0.5, expression of a *D. immitis* asparaginase protein was induced by addition of about 0.5 mM IPTG, followed by culture for about 3 hr at about 37° C. Protein production was monitored by SDS-PAGE of recombinant cell lysates, followed by Coomassie blue staining, using standard techniques. Recombinant cell *E. coli*:PTrc-nDiASNase$_{1770}$ produced a fusion protein, denoted herein as PHis-PDiASNase$_{590}$, that migrated with an apparent molecular weight of about 66 kD.

Immunoblot analysis of recombinant cell *E. coli*:PTrc-nDiASNase$_{1770}$ lysates indicated that an about 66 kD protein component of the cell lysates was able to bind a T$_7$ tag® monoclonal antibody (available from Novagen, Inc., Madison, Wis.) directed against the fusion portion of the recombinant PHis-PDiASNase$_{590}$ fusion protein. The PHis-PDiASNase590 histidine fusion protein was separated from *E. coli* proteins in cell lysates by cobalt chelation chromatography with an imidazole gradient elution. Immunoblot analysis of the *E. coli*:PTrc-nDiASNase$_{1770}$ lysates, column eluate and column void volume indicated that a 66 kD protein isolated from the *E. coli* lysates using cobalt column chromatography was able to selectively bind to the T$_7$ Tag® monoclonal antibody.

Example 8

This Example discloses the purification of a DiASNase fusion protein of the present invention from total cell lysates, and the production of antibody directed against the purified DiASNase fusion protein.

DiASNase fusion protein PHis-PDiASNase$_{590}$, produced as described in Example 7, was separated from *E. coli* proteins by Talon™ Metal Affinity Resin Chromatography (available from CLONTECH Laboratories, Inc., Palo Alto, Calif.) according to the manufacturer's instructions. The PHis-PDiASNase$_{590}$ fusion protein was eluted using an imidazole gradient, pooled and dialyzed against 1×PBS to produce cobalt column-purified PHis-PDiASNase590. The dialyzed protein was then concentrated using a 10K molecular weight cut off Centrifugal Ultra-free® concentrator (available from Millipore Corporation, Bedford, Mass.). The protein content of the fusion protein was determined by using a MicroBCA™ Protein Assay (available from Pierce, Rockford, Ill.). The purified protein was tested for its purity by SDS PAGE and immunoblot analysis.

Anti-PHis-PDiASNase$_{590}$ (anti-DiASNase) antisera was produced as follows: A rabbit was immunized subcutaneously, first with approximately 75 µg of the purified PHis-PDiASNase$_{590}$ protein with complete Freund's Adjuvant, and then with three subsequent immunizations of the same dose of the fusion protein mixed in Incomplete Freund's Adjuvant. Bleeding and immunization were performed at alternate weeks. Sera were separated and stored at −70° C. until use.

The immunoglobulin G (IgG) fraction from rabbit anti-DiASNase antisera (anti-DiASNase-IgG fraction) was collected by 50% ammonium sulfate precipitation. Ammonium ions were removed by extensive dialysis in 0.1 M PBS, pH 7.2. The IgG content was determined by measuring absorbance at OD$_{280}$ as compared with a blank PBS control. The anti-DiASNase-IgG fraction had a titer of 1:512,000 as determined by ELISA.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

SEQUENCE LISTING

The following Sequence Listing is submitted pursuant to 37 CFR §1.821. A copy in computer readable form is also submitted herewith.

Applicants assert pursuant to 37 CFR §1.821(f) that the content of the paper and computer readable copies of SEQ ID NO:1 through SEQ ID NO:26 submitted herewith are the same.

What is claimed is:

1. An isolated antibody that selectively binds to a protein comprising an amino acid sequence selected from the group consisting of SEQ ID NO:2, SEQ ID NO:7 and SEQ ID NO:12.

2. An isolated antibody that selectively binds to a protein wherein said protein is encoded by a nucleic acid molecule comprising a nucleic acid sequence selected from the group consisting of SEQ ID NO:1, SEQ ID NO:4, SEQ ID NO:6, SEQ ID NO:9, SEQ ID NO:11 and SEQ ID NO:25.

3. The antibody of claim 1, wherein said antibody is a monoclonal antibody.

4. The antibody of claim 1, wherein said antibody is a polyclonal antibody.

5. A composition comprising an excipient, a carrier, and an antibody wherein said antibody selectively binds to a protein comprising an amino acid sequence selected from the group consisting of SEQ ID NO:2, SEQ ID NO:7 and SEQ ID NO:12.

6. A composition comprising an excipient, a carrier, and an antibody, wherein said antibody selectively binds to a protein encoded by a nucleic acid molecule comprising a nucleic acid sequence selected from the group consisting of SEQ ID NO:1, SEQ ID NO:4, SEQ ID NO:6, SEQ ID NO:9, SEQ ID NO:11 and SEQ ID NO:25.

* * * * *